United States Patent
Homma et al.

(10) Patent No.: US 10,365,259 B2
(45) Date of Patent: Jul. 30, 2019

(54) HYDROGEN SENSOR INCLUDING PAIR OF ELECTRODES AND METAL OXIDE LAYER AND METHOD OF DETECTING HYDROGEN WITH HYDROGEN SENSOR

(71) Applicant: Panasonic Intellectual Property Management Co., Ltd., Osaka (JP)

(72) Inventors: Kazunari Homma, Kyoto (JP); Zhiqiang Wei, Osaka (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 85 days.

(21) Appl. No.: 15/446,960

(22) Filed: Mar. 1, 2017

(65) Prior Publication Data

US 2017/0269043 A1    Sep. 21, 2017

(30) Foreign Application Priority Data

Mar. 18, 2016    (JP) .................................. 2016-056115

(51) Int. Cl.
  *G01N 33/00*    (2006.01)
  *G01N 27/12*    (2006.01)

(52) U.S. Cl.
  CPC .......... *G01N 33/005* (2013.01); *G01N 27/125* (2013.01)

(58) Field of Classification Search
  CPC ............................ G01N 27/125; G01N 33/005
  USPC .................. 73/31.05, 31.06, 335.05; 422/83; 204/424–429
  See application file for complete search history.

(56) References Cited

U.S. PATENT DOCUMENTS

| | | | |
|---|---|---|---|
| 4,608,549 A | 8/1986 | Fukui | |
| 2005/0285155 A1* | 12/2005 | Johnson | G01N 27/129 257/253 |
| 2009/0026082 A1* | 1/2009 | Rothberg | C12Q 1/6869 204/556 |
| 2013/0250658 A1 | 9/2013 | Wei et al. | |

FOREIGN PATENT DOCUMENTS

| | | |
|---|---|---|
| JP | 59-120945 | 7/1984 |
| JP | 63-030751 | 2/1988 |
| JP | 2001-050923 | 2/2001 |
| JP | 2006-300560 | 11/2006 |

(Continued)

OTHER PUBLICATIONS

Song et al. AlGaN/GaN Schottky diode hydrogen sensor performance at high temperatures with different catalytic metals, Jul. 2005, ScienceDirect, Solid-State Electronics, 1330-1334 (Year: 2005).*

(Continued)

*Primary Examiner* — John Fitzgerald
*Assistant Examiner* — Truong D Phan
(74) *Attorney, Agent, or Firm* — McDermott Will & Emery LLP

(57) ABSTRACT

A hydrogen sensor includes: a first electrode; a second electrode; a metal oxide layer disposed between the first electrode and the second electrode and including a bulk area and a local area; a first insulation film covering the first electrode, the second electrode, and the metal oxide layer and having an opening reaching the second electrode; and a second insulation film being in contact with the second electrode in the opening.

18 Claims, 14 Drawing Sheets

(56) References Cited

FOREIGN PATENT DOCUMENTS

| JP | 2008-057976 | 3/2008 |
|---|---|---|
| WO | 2013/051267 | 4/2013 |

OTHER PUBLICATIONS

Yu et. al., Hydrogen gas sensing properties of Pt/Ta2O5 Schottky diodes based on Si and SiC substrates, Feb. 2011, SicenceDirect, Sensors and Actuators A: Physical, 9-14 (Year: 2011).*

B. Majkusiak et al., "Theoretical Limit for the SiO2 Thickness in Silicon Mos Devices", Science and Technology of Semiconductor-On-Insulator Structures and Devices Operating in a Harsh Environment, vol. 185 of the series NATO Science Series II: Mathematics, Physics and Chemistry, Apr. 2004, pp. 309-320.

* cited by examiner

HYDROGEN SENSOR INCLUDING PAIR OF ELECTRODES AND METAL OXIDE LAYER AND METHOD OF DETECTING HYDROGEN WITH HYDROGEN SENSOR

BACKGROUND

1. Technical Field

The present disclosure relates to a hydrogen sensor.

2. Description of the Related Art

A known hydrogen sensor disclosed in Japanese Examined Patent Application Publication No. 61-31422 includes a substrate, a Pt deposition film, a $SnO_2$ sintered compact, a $SiO_2$ film, and a heater. The $SiO_2$ film selectively transmits hydrogen molecules.

SUMMARY

In one general aspect, the techniques disclosed here feature a hydrogen sensor comprising: a first electrode; a second electrode; a metal oxide layer disposed between the first electrode and the second electrode and including a bulk area and a local area; a first insulation film covering the first electrode, the second electrode, and the metal oxide layer and having an opening reaching the second electrode; and a second insulation film being in contact with the second electrode in the opening.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
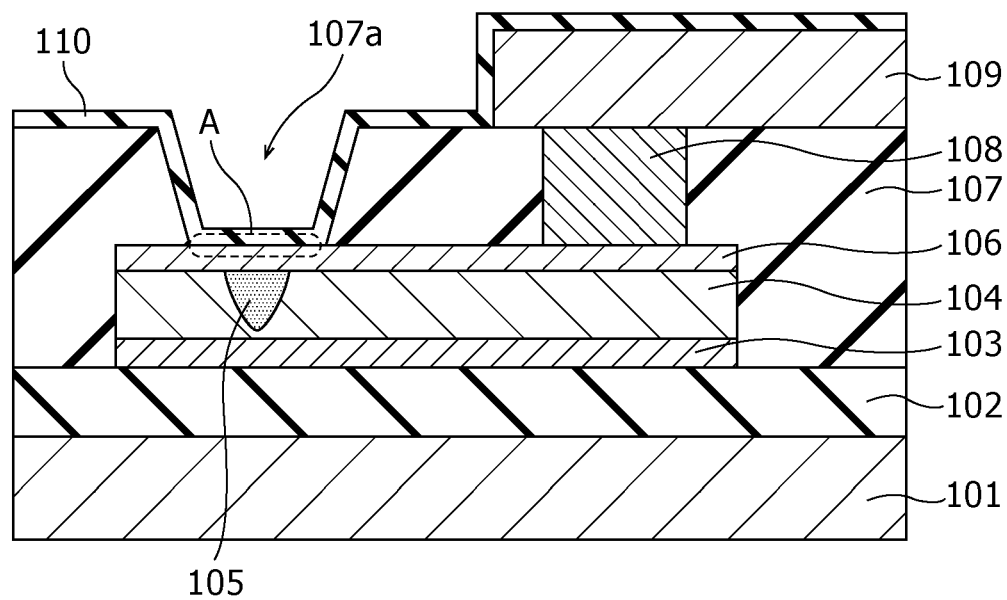
FIG. 1A is a cross-sectional view illustrating an example of the structure of a hydrogen sensor according to First Embodiment.

Embodiments of the present disclosure will now be described with reference to the drawings.

In the drawings, elements having substantially the same structures, behaviors, and effects are denoted by the same reference symbols, and duplicate explanations are omitted. The numerical values, materials, compositions, shapes, methods of forming films, and other factors described below are all examples for specifically describing embodiments of the present disclosure, and the present disclosure is not limited to these examples. Among the components in the following embodiments, the components not described in independent claims showing the highest-order concept will be described as arbitrary components.

In the present disclosure, the terms "first" and "second" are used for distinguishing similar components, not for describing temporal or spatial order. The terms "first" and "second" are appropriately exchangeable.

First Embodiment

[Structure of Hydrogen Sensor]

A hydrogen sensor according to First Embodiment is a gas sensor having a metal-insulator-metal (MIM) structure composed of a resistive film (metal oxide layer) and metal films and includes an insulation film on a metal disposed toward the gas as an object to be tested. The hydrogen sensor can detect hydrogen gas contained in combustible gas passed through the insulation film by utilizing self-heating and gas sensitivity at a local area formed in the resistive film with low power consumption without heating with a heater. Herein, the combustible gas is a gas containing, for example, hydrogen, carbon monoxide, methane, or alcohol. The hydrogen sensor can selectively detect hydrogen gas in combustible gas by including the insulation film made of a material selectively transmitting hydrogen gas.

FIG. 1A is a cross-sectional view illustrating an example of the structure of a hydrogen sensor 100 according to First Embodiment.

Figure 1B:
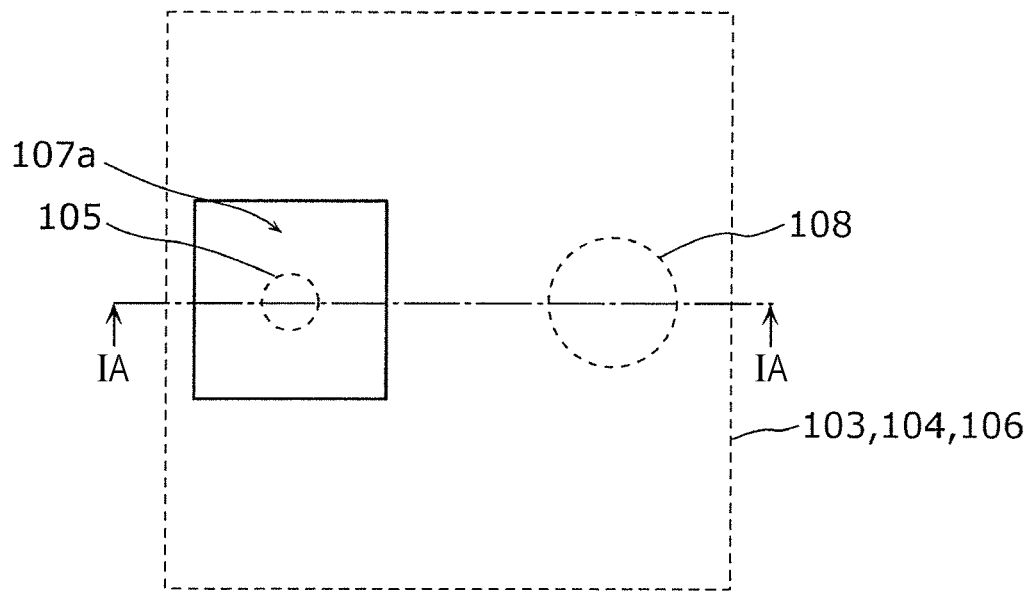
FIG. 1B is a top view illustrating the example of the structure of the hydrogen sensor according to First Embodiment.

FIG. 1B is a top view illustrating the example of the structure of the hydrogen sensor 100 according to First Embodiment. The cross-section shown in FIG. 1A corresponds to the cross-section viewed along the cutting line IA-IA of FIG. 1B in the arrow direction.

The hydrogen sensor 100 includes a substrate 101, an insulation film 102, a first electrode 103, a resistive film 104, a local area 105, a second electrode 106, an insulation film 107, a via 108, a wiring 109, and an insulation film 110. Herein, the resistive film 104 is a "metal oxide layer". The insulation film 107 and the insulation film 110 are a "first insulation film" and a "second insulation film", respectively.

The insulation film 102 is formed on the substrate 101. The first electrode 103 is disposed on the insulation film 102. The insulation film 107 is disposed on the second electrode 106. The insulation film 110 is disposed on the second electrode 106 and the insulation film 107.

The first electrode 103 and the second electrode 106 are disposed above the insulation film 102 such that their main surfaces face each other. The resistive film 104 is disposed so as to be in contact with the main surface of the first electrode 103 and the main surface of the second electrode 106.

The insulation film 107 is provided with an opening 107a for allowing hydrogen gas contained in the gas as an object to be tested to pass through the insulation film 110 and to reach the second electrode 106. In other words, the insulation film 107 covers the first electrode 103, the second electrode 106, and the resistive film 104 excluding the connection area A where the second electrode 106 and the insulation film 110 are in contact with each other. The upper surface of the insulation film 110 (i.e., the other surface opposite to the main surface being in contact with the second electrode 106) is exposed at least in the portion facing the connection area A.

The resistive film 104 is a layer lying between the first electrode 103 and the second electrode 106 and changing the resistance value based on the electrical signal applied between the first electrode 103 and the second electrode 106. Specifically, the resistive film 104 reversibly transitions between a high resistive state and a low resistive state depending on the voltage (potential difference) applied between the first electrode 103 and the second electrode 106. The hydrogen sensor 100 transitions from the high resistive state to the low resistive state depending on the hydrogen gas passed through the insulation film 110 and reached the second electrode 106.

The local area 105 is made of the same metal oxide as that for the resistive film 104 and is disposed in the inside of the resistive film 104 so as to be in contact with the second electrode 106 and not to be in contact with the first electrode 103. The degree of oxygen deficiency of the local area 105 is higher than that of its circumference (i.e., the bulk area of the resistive film 104). The degree of oxygen deficiency of the local area 105 reversibly changes depending on the electrical signal applied between the first electrode 103 and the second electrode 106. The local area 105 changes the degree of oxygen deficiency from a low state to a high state depending on the hydrogen gas passed through the insulation film 110 and reached the second electrode 106.

The local area 105 is a minute region in which a filament (conductive path) consisting of an oxygen defect site is inferred to be generated and disappear. The change in resistance of the resistive film 104 is inferred to be caused by generation or disappearance of the filament through a redox reaction occurred in the local area 105.

The insulation film 107 is provided with the via 108 passing through the insulation film 107 and being connected to the second electrode 106 in the portion covering the upper surface of the second electrode 106. The wiring 109 is disposed on the via 108.

The insulation film 110 has a function of selectively transmitting hydrogen gas. This function varies depending on the thickness of the insulation film 110. The term "selectively transmitting hydrogen gas" refers to transmitting hydrogen gas and substantially not transmitting gas other than hydrogen gas.

For example, if the insulation film 110 is a silicon oxide film having an excessively small thickness, electrons in the second electrode 106 passes through the silicon oxide film and leaks out. The leaked electrons may interact with molecules from the outside to cause, for example, absorption of the molecules or release of hydrogen atoms from the molecules.

The lower limit of the thickness for preventing gas other than hydrogen gas from transmitting is, for example, 0.5 nm calculated based on the disclosure in the literature written by B. Majkusiak, J. Walczak, et al. ("THEORETICAL LIMIT FOR THE $SiO_2$ THICKNESS IN SILICON MOS DEVICES", Science and Technology of Semiconductor-On-Insulator Structures and Devices Operating in a Harsh Environment, Volume 185 of the series NATO Science Series II: Mathematics, Physics and Chemistry, pp. 309-320).

Figure 2A:
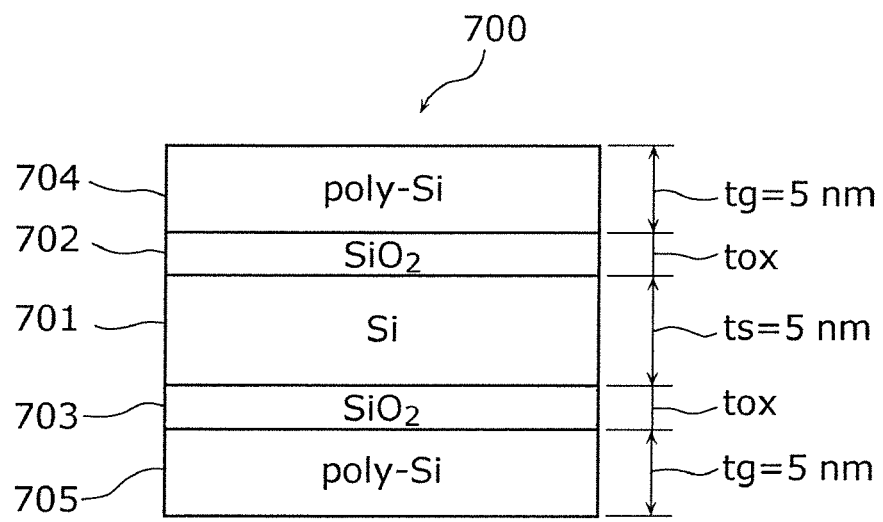
FIG. 2A is a cross-sectional view illustrating a double-gate silicon-on-insulator (DG SOI) structure.

FIG. 2A is a cross-sectional view of a structure 700 having a double-gate silicon-on-insulator (DG SOI) structure described in the above-mentioned literature. In the structure 700, silicon oxide films 702 and 703 are respectively deposited on the upper and lower main surfaces of the silicon substrate 701, and polysilicon films 704 and 705 are further respectively deposited thereon. For calculation, the thickness is of the silicon substrate 701 and the thickness tg of each of the polysilicon films are each adjusted to 5 nm, and the thickness tox of each of the silicon oxide films 702 and 703 is controlled.

Figure 2B:
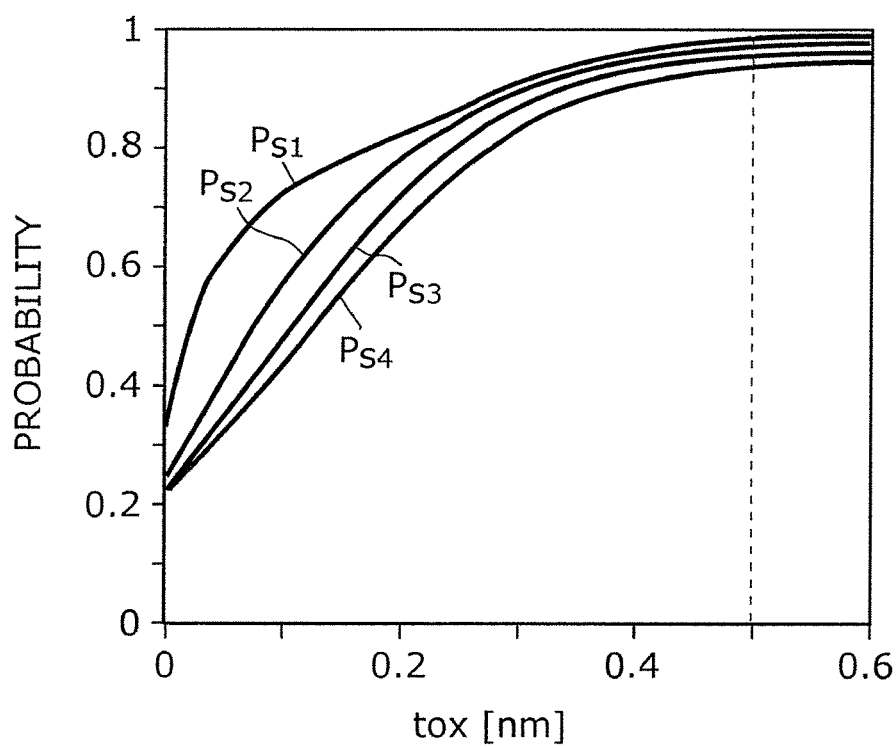
FIG. 2B is a graph showing a relationship between existence probability of electrons and silicon oxide film thickness.

FIG. 2B shows the results of existence probabilities ($P_{s1}$ to $P_{s4}$) of electrons in the silicon substrate 701 calculated by varying the thickness tox of each of the silicon oxide films 702 and 703 in the structure 700. Each of the lines Ps1 to Ps4 corresponds to the energy level of electrons in the substrate 701 of the DG-SOI structure shown in FIG. 2A. FIG. 2B shows the existence probability of electrons at each energy level. If the thickness tox is 0.5 nm or less, the existence probability of electrons in the silicon substrate 701 is considerably less than 1. This indicates that electrons in the silicon substrate 701 pass through the silicon oxide film 702 or 703 and leak out to the polysilicon film 704 or 705. If the thickness tox is 0.5 nm or more, the existence probability of electrons in the silicon substrate 701 is approximately 1. This indicates that electrons in the silicon substrate 701 cannot pass through the silicon oxide films 702 and 703 and do not leak out to the polysilicon films 704 and 705.

The results of calculation demonstrate that electrons cannot substantially pass through a silicon oxide film having a thickness tox of 0.5 nm or more. Accordingly, a silicon oxide film having a thickness of 0.5 nm or more deposited on the second electrode 106 can prevent the electrons in the second electrode 106 from interacting with molecules present in the outside. As a result, the gas in the outside is not adsorbed on the surface of the second electrode 106, and also hydrogen atoms are not released by the catalytic action of the second electrode 106 from the molecules containing hydrogen atoms.

In a silicon oxide film having an excessively large thickness, it takes a long time that hydrogen molecules pass through the silicon oxide film and reach the second electrode 106 to cause a change in resistance of the resistive film 104. Consequently, in order to achieve a desired response time, the silicon oxide film has an upper limit of the thickness. For example, the response time required in the hydrogen sensor to be used in a fuel-cell vehicle is within 1 second.

In the hydrogen sensor 100, the number of hydrogen molecules necessary for performing transition of the resistive film 104 from a high resistive state to a low resistive state varies depending on the material and the size of the hydrogen sensor 100. In an example of the hydrogen sensor investigated by the present inventors, the necessary number of hydrogen molecules is 2200. That is, in the hydrogen sensor, it is necessary that at least 2200 hydrogen molecules pass through the silicon oxide film and reach the second electrode 106 within 1 second.

When hydrogen gas having a hydrogen molecule density No is present on a surface of a silicon oxide film, the number n of hydrogen molecules passing through a silicon oxide film for t seconds is given by the following Expression 1:

$$n = N_O A \sqrt{\frac{\kappa_B T}{2nM}} \, \text{erfc}\left(\frac{x_1}{2\sqrt{D_{SiO2} L}}\right),$$

wherein
n: the number of hydrogen molecules passing through for t seconds;
$x_1$: silicon oxide film thickness;
$N_0$: hydrogen molecule density;
A: filament area;
$k_B$: Boltzmann constant;
T: Kelvin temperature;
M: hydrogen molecular mass;
$D_{SiO2}$: diffusion coefficient of hydrogen molecule (in $SiO_2$); and
t: time.

Figure 2C:
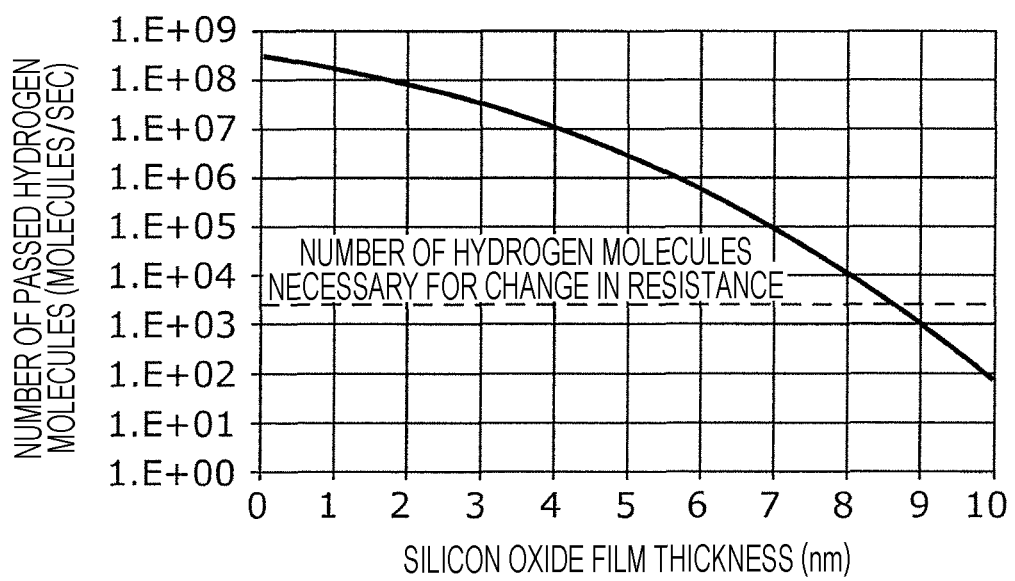
FIG. 2C is a graph showing a relationship between the number of hydrogen molecules passing through a silicon oxide film for 1 second and the thickness of the silicon oxide film.

FIG. 2C is a graph showing a relationship, calculated based on Expression 1, between the number of hydrogen molecules passing through a silicon oxide film for 1 second and the thickness of the silicon oxide film when the hydrogen molecule density $N_0$ is 0.1%. The broken line indicates the number, 2200, of hydrogen molecules necessary for a change in resistance of the resistive film 104, as an example. As obvious from FIG. 2C, a silicon oxide film having a thickness of 8.5 nm or less allows 2200 hydrogen molecules, which is necessary for a change in resistance, to reach the surface of the second electrode 106 within 1 second.

Theoretical resistance change behavior in the hydrogen sensor 100 will now be described.

In the present disclosure, the "degree of oxygen deficiency" of a metal oxide is a ratio of the amount of the oxygen deficit in the metal oxide to the amount of oxygen in the oxide having a stoichiometric composition consisting of the same elements as those of the metal oxide (herein, the amount of the oxygen deficit is the value obtained by subtracting the amount of oxygen in the metal oxide from the amount of oxygen in the metal oxide having a stoichiometric composition). If a plurality of metal oxides have a stoichiometric composition consisting of the same elements as those of the metal oxide, the degree of oxygen deficiency of the metal oxide is defined based on one having the highest resistance value among the metal oxides having the stoichiometric composition. The metal oxide having a stoichiometric composition is more stable and has a higher resistance value compared to metal oxides having other compositions.

For example, when the metal is tantalum (Ta), the oxide having the stoichiometric composition according to the above-described definition is $Ta_2O_5$ and can be expressed as $TaO_{2.5}$. The degree of oxygen deficiency of $TaO_{2.5}$ is 0%, and the degree of oxygen deficiency of $TaO_{1.5}$ is (2.5−1.5)/2.5, i.e., 40%. In an oxygen-excess metal oxide, the degree of oxygen deficiency is a negative value. In the present disclosure, the degree of oxygen deficiency can be a positive value, zero, or a negative value, unless otherwise specified.

An oxide having a low degree of oxygen deficiency is more similar to the oxide having a stoichiometric composition and therefore has a high resistance value, while an oxide having a high degree of oxygen deficiency is more similar to a metal constituting the oxide and therefore has a low resistance value.

The term "oxygen content" is the rate of the number of oxygen atoms based on the total number of all atoms. For example, the oxygen content of $Ta_2O_5$ is the rate (O/(Ta+O)) of the number of oxygen atoms based on the total number of all atoms, i.e., 71.4 atm %. Accordingly, an oxygen-deficient tantalum oxide has an oxygen content higher than 0 atm % and less than 71.4 atm %.

The local area 105 is formed in the resistive film 104 by applying an initial break voltage between the first electrode 103 and the second electrode 106. In other words, the initial break voltage is a voltage applied between the first electrode 103 and the second electrode 106 for forming the local area 105. The absolute value of the initial break voltage may be higher than that of the writing voltage. The writing voltage is a voltage applied between the first electrode 103 and the second electrode 106 for performing reversible transition between the high resistive state and the low resistive state of the resistive film 104. The absolute value of the initial break voltage may be less than that of the writing voltage. In such a case, the initial break voltage may be repeatedly applied or may be continuously applied for a predetermined period of time. As shown in FIG. 1A, the application of the initial break voltage forms a local area 105 being in contact with the second electrode 106 and not being in contact with the first electrode 103.

The local area 105 is conceived to contain a filament (conductive path) consisting of an oxygen defect site. The local area 105 has a minute size matching with the filament necessary for current to flow. The formation of the filament in the local area 105 will be described using a percolation model.

The percolation model is based on a theory that a density of oxygen defect sites exceeding a threshold increases the probability of forming a connection of oxygen defect sites in an assumed random distribution of the oxygen defect sites in the local area 105.

In the percolation model, a filament is formed by connection of a plurality of oxygen defect sites in the local area 105. The change in resistance of the resistive film 104 is caused through generation and disappearance of oxygen defect sites in the local area 105.

Herein, the term "oxygen defect" refers to that oxygen in a metal oxide is deficient compared to that of the stoichiometric composition. The term "density of oxygen defect sites" corresponds to the degree of oxygen deficiency. That is, the density of oxygen defect sites increases with the degree of oxygen deficiency.

The local area 105 may be formed at only one region of the resistive film 104 of the hydrogen sensor 100. The number of local areas 105 formed in the resistive film 104 can be determined by, for example, electron beam absorbed current (EBAC) analysis.

When the local area 105 is present in the resistive film 104, the current flowing in the resistive film 104 by application of a voltage between the first electrode 103 and the second electrode 106 is concentrated in the local area 105.

The local area 105 has a small size and therefore generates heat by, for example, a current of about several tens of microamperes flowing at the time of reading out the resistance value. This heat generation causes a considerable increase in the temperature. The power consumption when a current of about several tens of microamperes flows is less than 0.1 mW.

The second electrode 106 is made of a metal (e.g., Pt) having a catalytic action, and the local area 105 is in contact with the second electrode 106. In this structure, the second electrode 106 is heated by the heat generated in the local area 105 to efficiently release hydrogen atoms form hydrogen gas.

If the gas as an object to be tested contains hydrogen gas, hydrogen atoms are released from the hydrogen gas at the second electrode 106, and the released hydrogen atoms bind to oxygen atoms in the local area 105 to reduce the resistance value of the local area 105.

The hydrogen sensor 100 thus has characteristics of decreasing the resistance value between the first electrode 103 and the second electrode 106 when hydrogen gas is brought into contact with the second electrode 106. Such characteristics allow the detection of hydrogen gas contained in the gas as an object to be tested by detecting a reduction in the resistance value between the first electrode 103 and the second electrode 106 when the gas is brought into contact with the second electrode 106.

Furthermore, even if the local area 105 is in any of the high resistive state and the low resistive state, a further reduction in the resistance value is caused by bringing hydrogen gas into contact with the second electrode 106. Accordingly, the hydrogen sensor 100 can detect hydrogen gas, even if the local area 105 is in any of the high resistive state and the low resistive state. However, in order to more clearly detect a reduction in the resistance value, the local area 105 may be electrically set to a high resistive state, previous to the use of the hydrogen sensor 100.

The details of the hydrogen sensor 100 for obtaining stable resistance change characteristics will now be described.

The resistive film 104 is made of an oxygen-deficient metal oxide. The mother metal of the metal oxide may be at least one selected from transition metals, such as tantalum (Ta), hafnium (Hf), titanium (Ti), zirconium (Zr), niobium (Nb), tungsten (W), nickel (Ni), and iron (Fe); and aluminum (Al). Since transition metals have multiple oxidation states, different resistive states can be achieved by a redox reaction.

Herein, the term "oxygen-deficient metal oxide" refers to a metal oxide having a higher degree of oxygen deficiency compared to a metal oxide having the stoichiometric composition of the same metal elements. The oxygen-deficient metal oxide typically has semiconductor characteristics, while the metal oxide having the stoichiometric composition is typically an insulator. A hydrogen sensor 100 having a resistive film 104 made of an oxygen-deficient metal oxide can achieve high reproducibility and stable resistance change behavior.

For example, when the metal oxide constituting the resistive film 104 is hafnium oxide represented by $HfO_x$ in which the value x is 1.6 or more, the resistive film 104 can stably change the resistance value. In such a case, the hafnium oxide film may have a thickness of 3 to 4 nm.

When the metal oxide constituting the resistive film 104 is zirconium oxide represented by $ZrO_x$ in which the value of x is 1.4 or more, the resistive film 104 can stably change the resistance value. In such a case, the zirconium oxide film may have a thickness of 1 to 5 nm.

When the metal oxide constituting the resistive film 104 is tantalum oxide represented by $TaO_x$ in which the value of x is 2.1 or more, the resistive film 104 can stably change the resistance value.

The compositions of the above-mentioned metal oxide layers can be measured by Rutherford backscattering spectrometry.

The materials for the first electrode 103 and the second electrode 106 are selected from, for example, platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), and titanium aluminum nitride (TiAlN).

Specifically, the second electrode 106 is constituted of a material having a catalytic action of releasing hydrogen atoms from gas molecules including hydrogen atoms, such as platinum (Pt), iridium (Ir), and palladium (Pd). The first electrode 103 may be constituted of a material having a standard electrode potential less than that of the metal constituting the metal oxide, such as tungsten (W), nickel (Ni), tantalum (Ta), titanium (Ti), aluminum (Al), tantalum nitride (TaN), and titanium nitride (TiN). A material having a higher value of the standard electrode potential is more difficult to be oxidized.

The substrate 101 may be any substrate and is, for example, a silicon single crystal substrate or a semiconductor substrate. The resistive film 104 can be formed at a relatively low substrate temperature. For example, the resistive film 104 can also be formed on a material such as a resin material.

The hydrogen sensor 100 may further include a load element electrically connected to the resistive film 104, such as a fixed resistance, a transistor, or a diode.

Furthermore, the hydrogen sensor 100 may include a measurement circuit for measuring the current flowing in the resistive film 104 when a predetermined voltage is applied between the first electrode 103 and the second electrode 106. The hydrogen sensor 100 may include a power supply circuit for applying a predetermined voltage at all times between the first electrode 103 and the second electrode 106. Such a structure can provide a hydrogen sensor having high convenience as a module component including a measurement circuit or a power supply circuit.

[Manufacturing Process and Operation of Hydrogen Sensor]

An example of a process of producing the hydrogen sensor 100 will now be described with reference to FIGS. 3A to 3G.

Figure 3A:
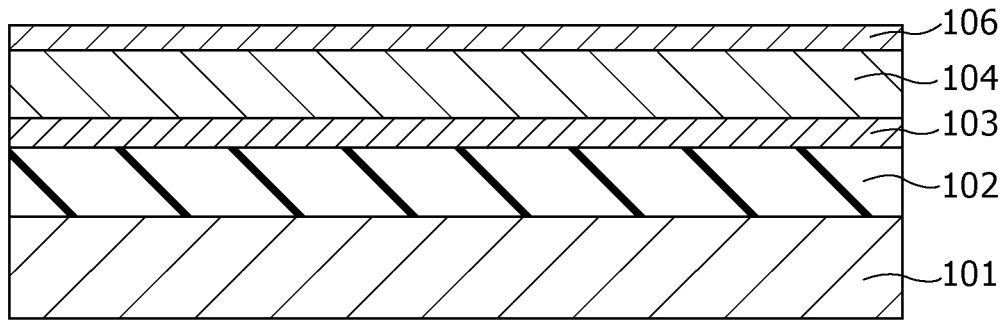
FIG. 3A is a cross-sectional view illustrating an example of a process of producing the hydrogen sensor according to First Embodiment.

First, as shown in FIG. 3A, an insulation film 102 having a thickness of 200 nm is formed on a substrate 101, for example, of single crystal silicon by a thermal oxidation method. Subsequently, a first electrode 103 of, for example, a Pt thin film having a thickness of 100 nm is formed on the insulation film 102 by sputtering. In addition, an adhesion layer of, for example, Ti or TiN may be formed between the first electrode 103 and the insulation film 102 by sputtering. An oxygen-deficient metal oxide layer, which becomes a resistive film 104, is then formed on the first electrode 103 by reactive sputtering using, for example, a Ta target. A resistive film 104 is thus formed.

Herein, the thickness of the resistive film 104 may be, for example, about 1 nm or more and about 8 nm or less for appropriately reducing the initial resistance value and securing stable resistance change characteristics.

Subsequently, a second electrode 106 of, for example, a Pt thin film having a thickness of 150 nm is formed on the resistive film 104 by sputtering.

Figure 3B:
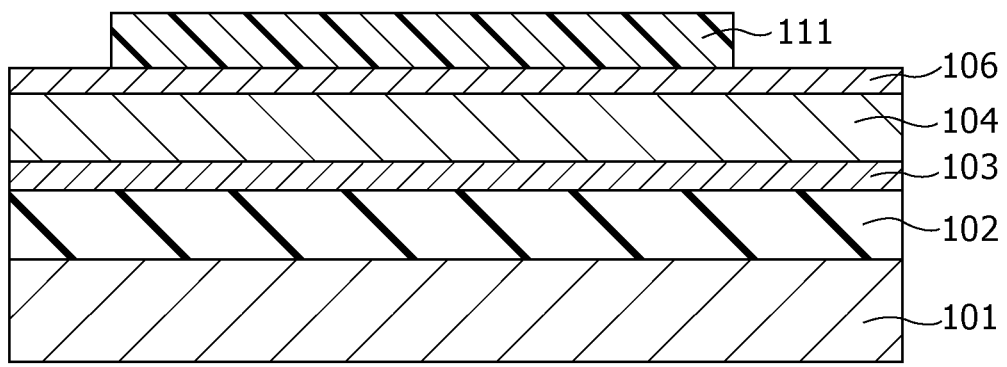
FIG. 3B is a cross-sectional view illustrating an example of the process of producing the hydrogen sensor according to First Embodiment.
Figure 3C:
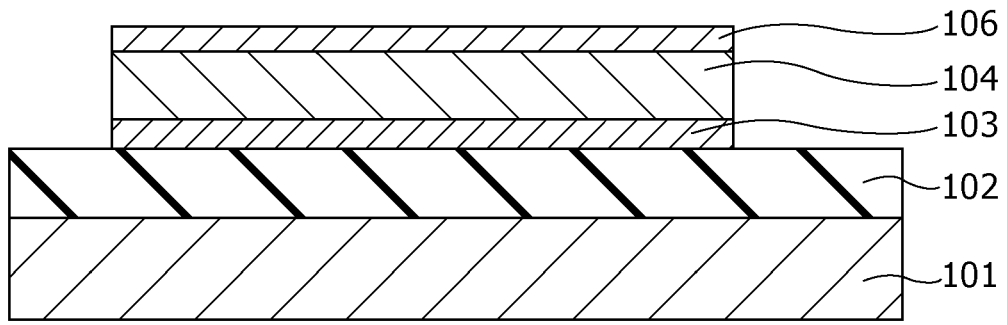
FIG. 3C is a cross-sectional view illustrating an example of the process of producing the hydrogen sensor according to First Embodiment.

Subsequently, as shown in FIG. 3B, a photoresist mask 111 is formed by a photolithography process. Then, as shown in FIG. 3C, the first electrode 103, the resistive film 104, and the second electrode 106 are formed into the shape of the device by dry etching using the mask 111.

Figure 3D:
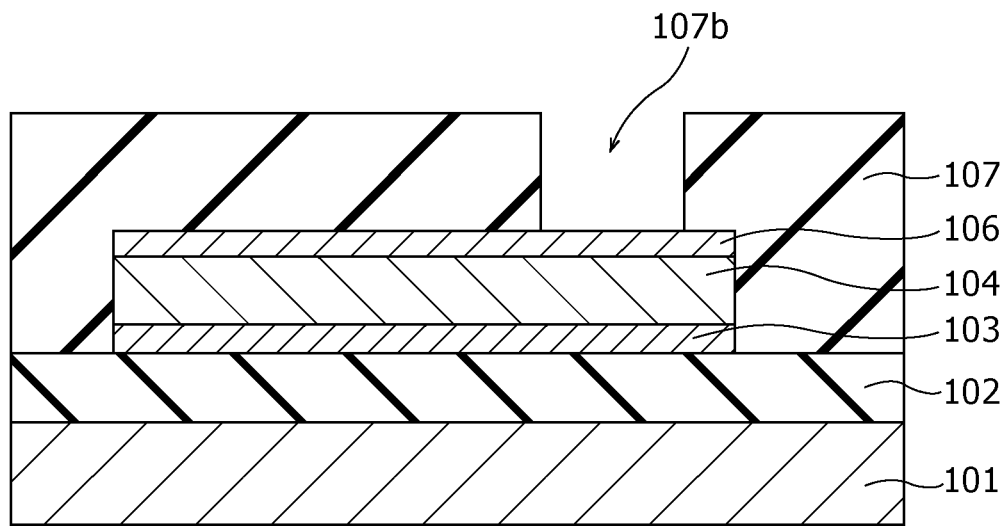
FIG. 3D is a cross-sectional view illustrating an example of the process of producing the hydrogen sensor according to First Embodiment.

Then, as shown in FIG. 3D, an insulation film 107 is formed so as to cover the insulation film 102, the first electrode 103, the resistive film 104, and the second electrode 106. A via hole 107b reaching a part of the upper surface of the second electrode 106 is then formed by etching the insulation film 107.

Figure 3E:
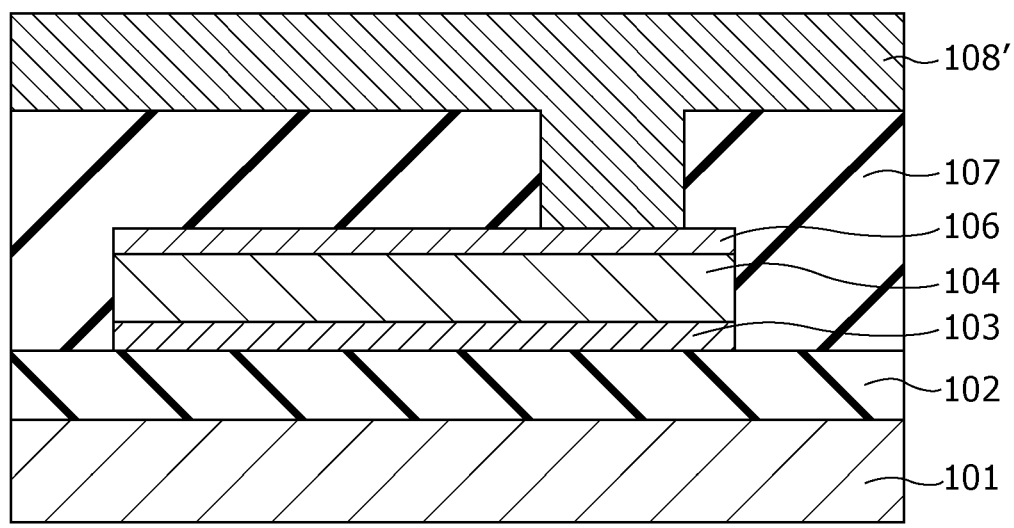
FIG. 3E is a cross-sectional view illustrating an example of the process of producing the hydrogen sensor according to First Embodiment.
Figure 3F:
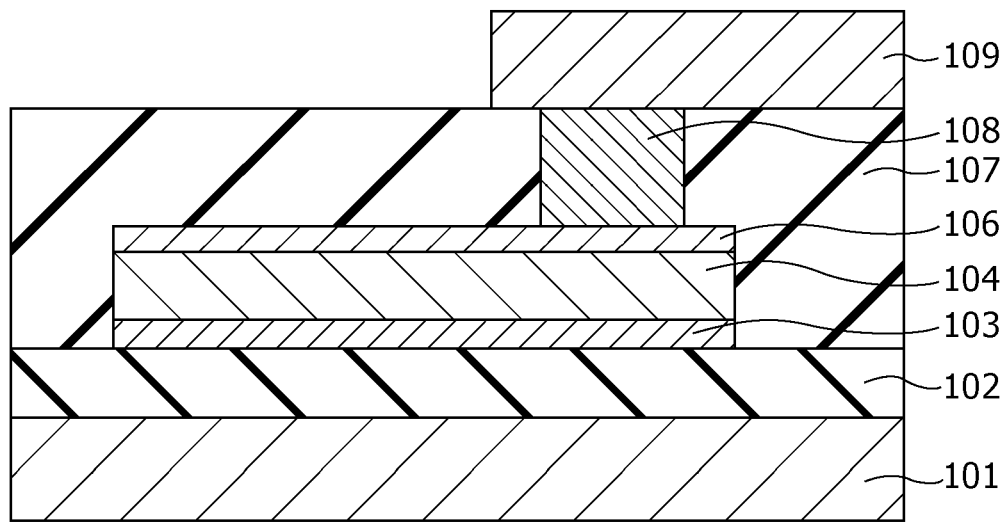
FIG. 3F is a cross-sectional view illustrating an example of the process of producing the hydrogen sensor according to First Embodiment.

Subsequently, as shown in FIG. 3E, a conductor film 108' is formed on the upper surface of the insulation film 107 and the inside of the via hole 107b so as to fill the via hole 107b. Then, as shown in FIG. 3F, the conductor film 108' on the insulation film 107 is removed by chemical mechanical planarization (CMP) to form a via 108 in the via hole 107b. Another conductor film is further formed on the insulation film 107 and is patterned to form a wiring 109 connected to the via 108.

Figure 3G:
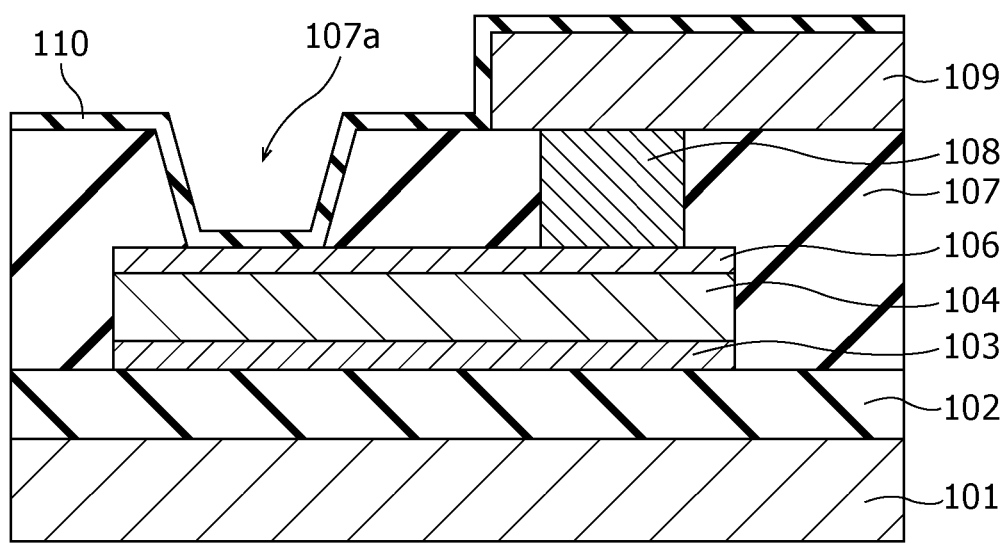
FIG. 3G is a cross-sectional view illustrating an example of the process of producing the hydrogen sensor according to First Embodiment.

Subsequently, as shown in FIG. 3G, an opening 107a exposing a part of the upper surface of the second electrode 106 is formed by etching the insulation film 107, and an insulation film 110 having a thickness ranging from 0.5 nm to 8.5 nm is then deposited.

Subsequently, an initial break voltage is applied between the first electrode 103 and the second electrode 106 to form a local area 105 shown in FIG. 1A in the resistive film 104. A hydrogen sensor 100 is thus produced by the process described above.

An example of the resistance change characteristics by voltage application in the hydrogen sensor 100 will be described by the results of actual measurement using a sample device. The resistance change characteristics by hydrogen gas in the hydrogen sensor 100 will now be described.

Figure 4:
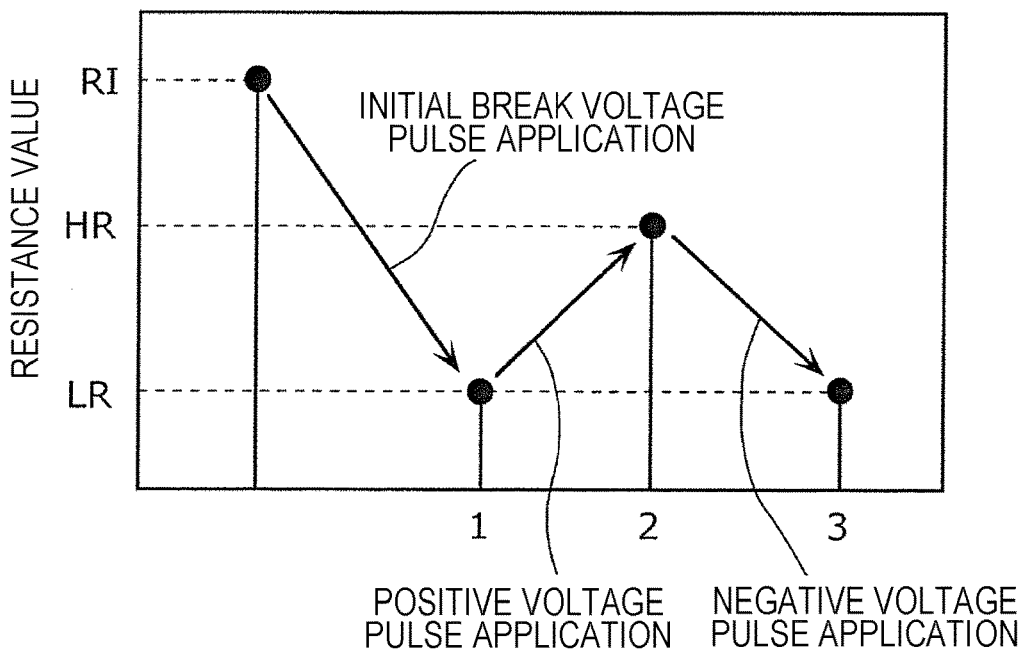
FIG. 4 is a graph showing an example of the transition in the resistive state of the hydrogen sensor according to First Embodiment.

FIG. 4 is a graph showing the resistance change characteristics actually measured using a sample device.

In the hydrogen sensor 100 as the sample device giving the measurement results shown in FIG. 4, the first electrode 103, the second electrode 106, and the resistive film 104 each have a size of 0.5 μm×0.5 μm (area: 0.25 μm$^2$); the value of y of TaOy representing the composition of tantalum oxide constituting the resistive film 104 is 2.47; and the resistive film 104 has a thickness of 5 nm. In this hydrogen sensor 100, if a read-out voltage (e.g., 0.4 V) is applied between the first electrode 103 and the second electrode 106, the initial resistance value RI is about $10^7$ to $10^8 \Omega$.

As shown in FIG. 4, if the resistance value of the hydrogen sensor 100 is an initial resistance value RI (a value higher than the resistance value HR in a high resistive state), the resistive state changes by applying an initial break voltage between the first electrode 103 and the second electrode 106. The resistance value of the resistive film 104 changes as shown in FIG. 4 by alternately applying, for example, two kinds of voltage pulses having different polarities (a positive voltage pulse and a negative voltage pulse) and each having a pulse width of 100 ns as a write-in voltage between the first electrode 103 and the second electrode 106 of the hydrogen sensor 100.

That is, a positive voltage pulse (pulse width: 100 ns) as the write-in voltage applied between the electrodes increases the resistance value of the resistive film 104 from the low resistance value LR to the high resistance value HR. In contrast, a negative voltage pulse (pulse width: 100 ns) as the write-in voltage applied between the electrodes decreases the resistance value of the resistive film 104 from the high resistance value HR to the low resistance value LR. The polarity of a voltage pulse is "positive" when the potential of the second electrode 106 is higher than that of the first electrode 103 as a reference, and is "negative" when the potential of the second electrode 106 is less than that of the first electrode 103 as a reference.

Before the start of monitoring of hydrogen gas, a positive voltage pulse is applied between the first electrode 103 and the second electrode 106. As a result, hydrogen gas can be detected with the hydrogen sensor 100 set to the high resistive state (HR). In such a case, a reduction in resistance value can be more clearly detected, compared to the detection of hydrogen gas using the hydrogen sensor 100 in a low resistive state (LR), resulting in an improvement in the characteristics of detecting hydrogen gas.

[Modification]

Figure 5:
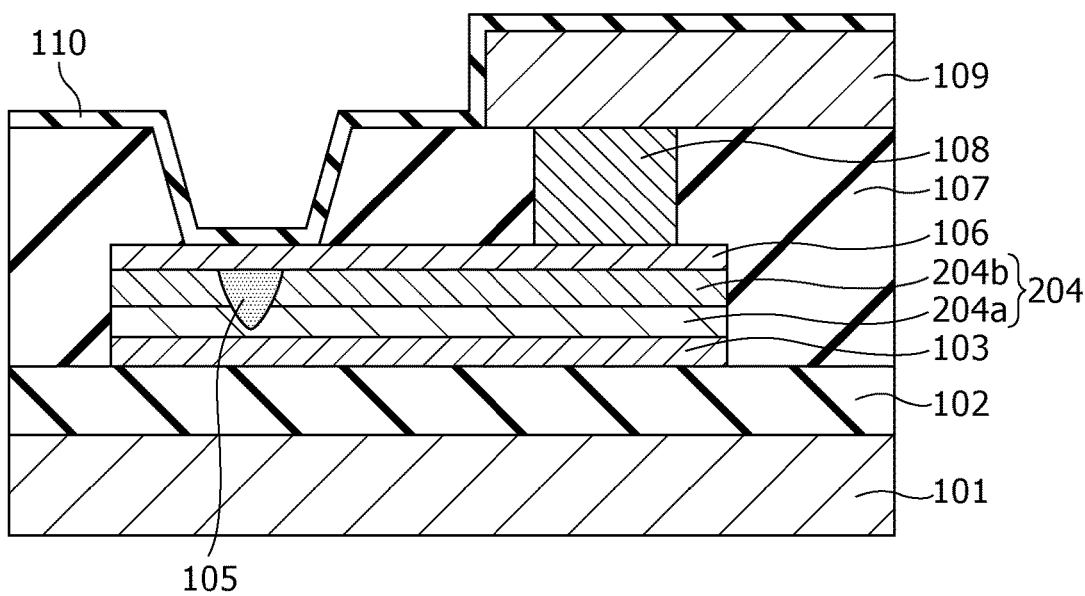
FIG. 5 is a cross-sectional view illustrating the structure of a hydrogen sensor according to a modification of First Embodiment.

FIG. 5 is a cross-sectional view illustrating an example of the structure of a hydrogen sensor according to a modification of First Embodiment. Only the points different from the hydrogen sensor 100 of First Embodiment will now be described.

The hydrogen sensor 200 of the modification differs from the hydrogen sensor 100 of First Embodiment in that the resistive film 204 includes a first metal oxide layer 204a being in contact with the first electrode 103 and a second metal oxide layer 204b being in contact with the second electrode 106. The resistive film 204 is not limited to a layered product of two layers and may be a layered product of three or more layers.

The first metal oxide layer 204a and the second metal oxide layer 204b include a local area 105 that reversibly changes the degree of oxygen deficiency depending on application of an electric pulse and hydrogen gas. The local area 105 at least passes through the second metal oxide layer 204b and is in contact with the second electrode 106.

In other words, the resistive film 204 includes a layered structure at least composed of a first metal oxide layer 204a containing a first metal oxide and a second metal oxide layer 204b containing a second metal oxide. The first metal oxide layer 204a is disposed between the first electrode 103 and the second metal oxide layer 204b, and the second metal oxide layer 204b is disposed between the first metal oxide layer 204a and the second electrode 106.

The second metal oxide layer 204b may have a thickness smaller than that of the first metal oxide layer 204a. In such a case, a structure including the local area 105 not being in contact with the first electrode 103 can be readily formed. The degree of oxygen deficiency of the second metal oxide layer 204b may be less than that of the first metal oxide layer 204a. In such a case, the resistance value of the second metal oxide layer 204b is higher than that of the first metal oxide layer 204a. Accordingly, most of the voltage applied to the resistive film 204 is applied to the second metal oxide layer 204b. This structure is advantageous for, for example, concentrating the initial break voltage in the second metal oxide layer 204b and reducing the initial break voltage necessary for forming the local area 105.

In the present disclosure, if the metals constituting the first metal oxide layer 204a and the second metal oxide layer 204b are the same, the term "oxygen content" may be used instead of the term "degree of oxygen deficiency". "High oxygen content" corresponds to "low degree of oxygen deficiency", and "low oxygen content" corresponds to "high degree of oxygen deficiency".

However, as described below, the resistive film 204 according to this embodiment is not limited to the case that the metals constituting the first metal oxide layer 204a and the second metal oxide layer 204b are the same, and the metals may be different from each other. That is, the first metal oxide layer 204a and the second metal oxide layer 204b may be made of different metal oxides.

If the first metal constituting the first metal oxide layer 204a and the second metal constituting the second metal oxide layer 204b are the same, the oxygen content has a corresponding relationship with the degree of oxygen deficiency. That is, when the oxygen content of the second metal oxide is higher than that of the first metal oxide, the second metal oxide has a degree of oxygen deficiency less than that of the first metal oxide.

The resistive film 204 includes a local area 105 in the vicinity of the interface between the first metal oxide layer 204a and the second metal oxide layer 204b. The local area 105 has a degree of oxygen deficiency higher than that of the second metal oxide layer 204b and is different from that of the first metal oxide layer 204a.

The local area 105 is formed in the resistive film 204 by applying an initial break voltage between the first electrode 103 and the second electrode 106. The initial break voltage forms the local area 105 that is in contact with the second electrode 106, passes through the second metal oxide layer 204b, partially penetrates into the first metal oxide layer 204a, and is not in contact with the first electrode 103.

An example of evaluation of the resistance change characteristics of the thus-structured hydrogen sensor 200 by hydrogen gas will be described.

Figure 6A:
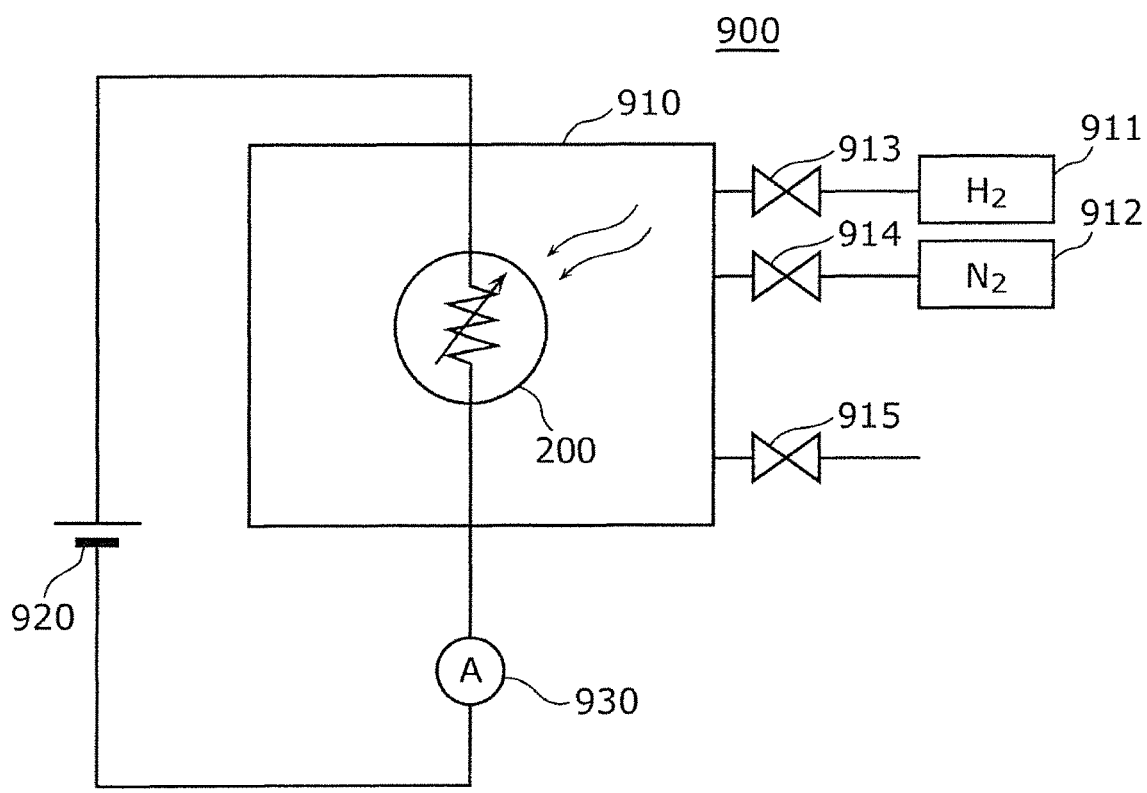
FIG. 6A is a diagram illustrating an evaluation system of a hydrogen sensor according to a modification of First Embodiment.

FIG. 6A is a block diagram illustrating an example of an evaluation system used for evaluating the hydrogen sensor 200. The evaluation system 900 shown in FIG. 6A includes an airtight container 910 accommodating the hydrogen sensor 200, a power supply 920, and a current meter 930. The airtight container 910 is connected to a hydrogen cylinder 911 and a nitrogen cylinder 912 through introduction valves 913 and 914, respectively, and is configured such that the gas in the inside can be exhausted through an exhaust valve 915.

Figure 6B:
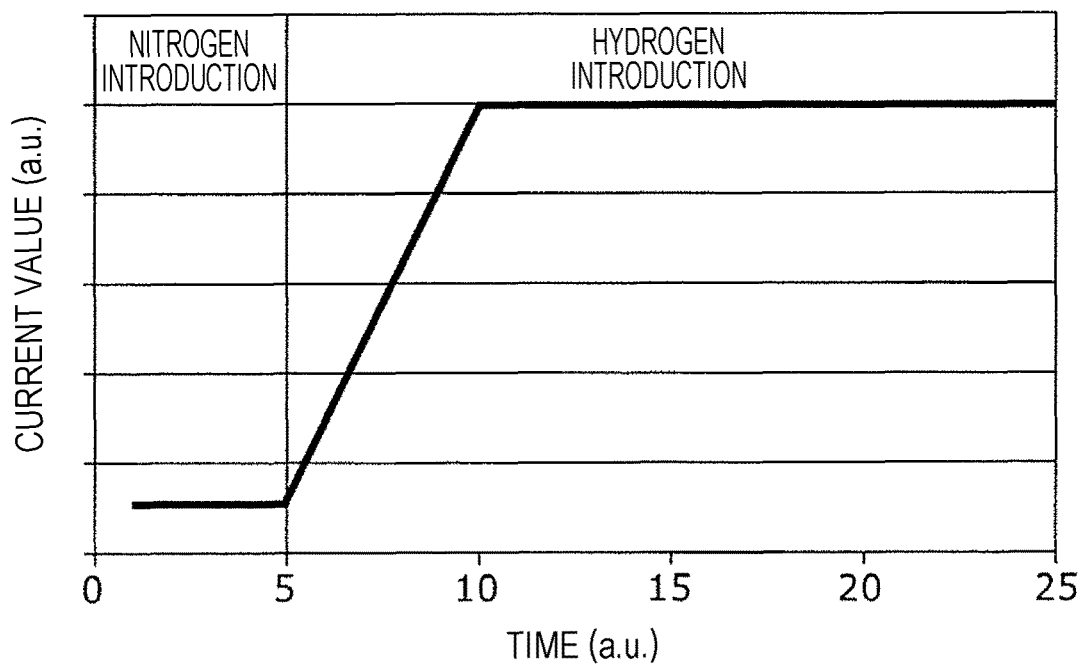
FIG. 6B is a graph showing the results of evaluation of a hydrogen sensor according to a modification of First Embodiment.

FIG. 6B is a graph showing an example of evaluation of the hydrogen sensor 200. The horizontal axis indicates the time (sec), and the vertical axis indicates the value (a.u.) of current flowing between the first electrode 103 and the second electrode 106. In the experiment, nitrogen gas was introduced into the airtight container 910 accommodating the hydrogen sensor 200, and hydrogen gas was then introduced thereinto. FIG. 6B shows the results of the experiment. The horizontal axis indicates the two periods for carrying out the introduction of nitrogen and the introduction of hydrogen. The current value started to increase after the change of the introduction gas from nitrogen gas to hydrogen gas, and the current was saturated within 1 second from the introduction of hydrogen gas (In FIG. 6B, the time on the horizontal axis is shown in an arbitrary unit (a.u.)).

In this example of evaluation, a predetermined voltage (potential difference) was applied between the first electrode 103 and the second electrode 106 to set the local area 105 to a high resistive state in advance. In the monitoring behavior for hydrogen gas, a detection voltage of 0.6 V was applied between the first electrode 103 and the second electrode 106. In the state that hydrogen gas was detected, a current of 10 to 20 µA flowed between the first electrode 103 and the second electrode 106. It is therefore demonstrated that the hydrogen sensor 200 can monitor hydrogen gas with a very small power consumption of 0.006 to 0.012 mW at the highest.

When a detection voltage of 0.4 V was applied between the first electrode 103 and the second electrode 106, hydrogen gas did not cause a change in resistance and was not detected. This was probably caused by that the amount of the heat generated in the local area 105 by application of a detection voltage of 0.4 V was insufficient and the catalytic action of the second electrode 106 was not sufficiently accelerated. It is inferred that in order to detect hydrogen gas, for example, a detection voltage of 0.6 V was necessary to be applied.

Figure 6C:
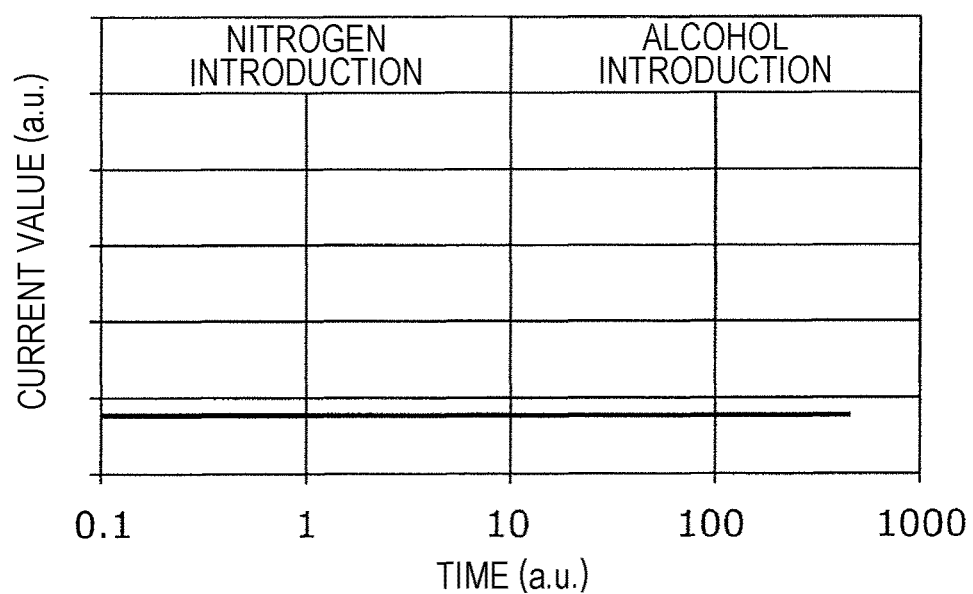
FIG. 6C is a graph showing the results of evaluation of a hydrogen sensor according to a modification of First Embodiment.

FIG. 6C is a graph showing an example of evaluation of the hydrogen sensor 200. The horizontal axis indicates the time (sec), and the vertical axis indicates the value (a.u.) of current flowing between the first electrode 103 and the second electrode 106. In the experiment, nitrogen gas was introduced into the airtight container 910 accommodating the hydrogen sensor 200, and alcohol gas was then introduced thereinto.

FIG. 6C shows the results of the experiment. The horizontal axis indicates the two periods for carrying out the introduction of nitrogen and the introduction of alcohol. It is demonstrated that the change of the introduction gas from nitrogen gas to alcohol gas does not cause a flow of current.

In this example of evaluation, a predetermined voltage (potential difference) was applied between the first electrode 103 and the second electrode 106 to set the local area 105 to a high resistive state in advance. In the monitoring behavior for hydrogen gas, a detection voltage of 0.6 V was applied between the first electrode 103 and the second electrode 106, but the hydrogen sensor 200 did not show a reaction against alcohol.

From the results described above, the inventors presume the mechanism of detecting hydrogen gas and the mechanism of not reacting with alcohol in the hydrogen sensor 200 as follows.

In the hydrogen sensor 200, the current value was saturated within 1 second from the introduction of hydrogen. It is therefore inferred that the number of hydrogen molecules passing through the insulation film 110 within 1 second is higher than that necessary for changing the resistance of the resistive film 104. In contrast, the hydrogen sensor 200 did not show a reaction against alcohol gas. It is therefore inferred that alcohol molecules do not pass through the insulation film 110 and are not brought into contact with the second electrode 106. The insulation film 110 thus has selectivity of readily transmitting hydrogen gas and hardly transmitting gas other than hydrogen.

The contact of the hydrogen gas passed through the insulation film 110 with the second electrode 106 causes a release of hydrogen atoms from the hydrogen gas by the catalytic action of the second electrode 106. The released hydrogen atoms diffuse in the second electrode 106 for maintaining the equilibrium state and reach the local area.

It is inferred that these hydrogen atoms cause a redox reaction in the minute local area 105 to increase the degree of oxygen deficiency in the local area 105; as a result, the filaments in the local area 105 are readily connected to one another to reduce the resistance value of the local area 105; and as a result, the current flowing between the first electrode 103 and the second electrode 106 is increased.

It is inferred that the above-described behavior is not limited to the hydrogen sensor 200 and also occurs in the hydrogen sensor 100 and other hydrogen sensors described below, these sensors having substantially the same structures of the main sections as that of the main section of the hydrogen sensor 200.

As described above, in the hydrogen sensors 100 and 200 according to the embodiments, the insulation film 110 selectively transmits hydrogen gas, and thereby these hydrogen sensors selectively detect hydrogen gas. The hydrogen sensors can generate heat by only the current for detecting the resistive state and can detect hydrogen gas without heating with a separate heater. Thus, a hydrogen sensor having excellent power-saving properties can be given.

[Supplement]

In FIG. 1A, the hydrogen sensor 100 includes a first electrode 103, a metal oxide layer 104, a second electrode 106, a first insulation film 107, and a second insulation film 110.

The metal oxide layer 104 includes a local area 105. In the metal oxide layer 104, the area surrounding the local area 105 is called a bulk area. Herein, the term "surrounding the local area 105" is not limited to entirely surrounding the outer periphery of the local area 105. The degree of oxygen deficiency of the local area 105 is higher than that of the bulk area.

The first insulation film 107 covers the first electrode 103, the metal oxide layer 104, and the second electrode 106. The first insulation film 107 includes an opening 107a reaching the second electrode 106.

The second insulation film 110 covers the first insulation film 107 and the second electrode 106 in the opening 107. The second insulation film 110 is in contact with the upper surface of the first insulation film 107, the inner peripheral surface of the opening 107, and a part of the upper surface of the second electrode 106. The second insulation film 110 has a thickness smaller than that of the first insulation film 107. The second insulation film 110 includes a planar portion and a bottomed cylindrical portion. The second insulation film 110 is, for example, a silicon oxide film, a silicon nitride film, a silicon oxynitride film, or an aluminum oxide film.

As shown in FIG. 1B, the local area 105 lies in the inside of the opening 107a, when viewed from a direction perpendicular to the main surface of the second electrode 106. In other words, as shown in FIG. 1A, the second insulation film 110, the second electrode 106, and the local area 105 are disposed in this order in a direction passing through the opening 107a.

In FIG. 1A, the hydrogen sensor 100 includes a conductive plug 108 passing through the first insulation film 107 and connected to the second electrode 106 and a wiring 109 connected to the conductive plug 108. In FIG. 1A, the second insulation film 110 covers the conductive plug 108 and the wiring 109.

Second Embodiment

[Structure of Hydrogen Sensor]

A hydrogen sensor according to Second Embodiment is, as in the hydrogen sensor according to First Embodiment, a gas sensor having a metal-insulation film-metal (MIM) lamination structure composed of a resistive film (metal oxide layer) and metal films and includes an insulation film on a metal disposed toward the gas as an object to be tested. The hydrogen sensor can detect hydrogen gas contained in combustible gas passed through the insulation film by utilizing self-heating and gas sensitivity at a local area formed in the resistive film with low power consumption without heating with a heater. Herein, the combustible gas is, for example, gas containing hydrogen, carbon monoxide, methane, alcohol, etc. The hydrogen sensor can selectively detect hydrogen gas by constituting the insulation film by a material that selectively transmits hydrogen gas.

Figure 7A:
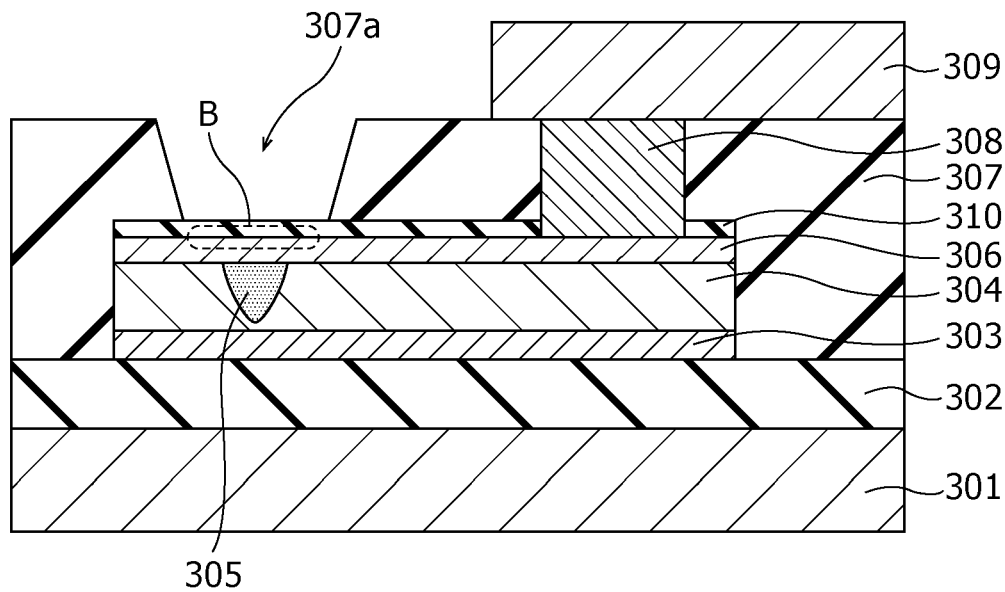
FIG. 7A is a cross-sectional view illustrating an example of the structure of a hydrogen sensor according to Second Embodiment.

FIG. 7A is a cross-sectional view illustrating an example of the structure of a hydrogen sensor 300 according to Second Embodiment.

Figure 7B:
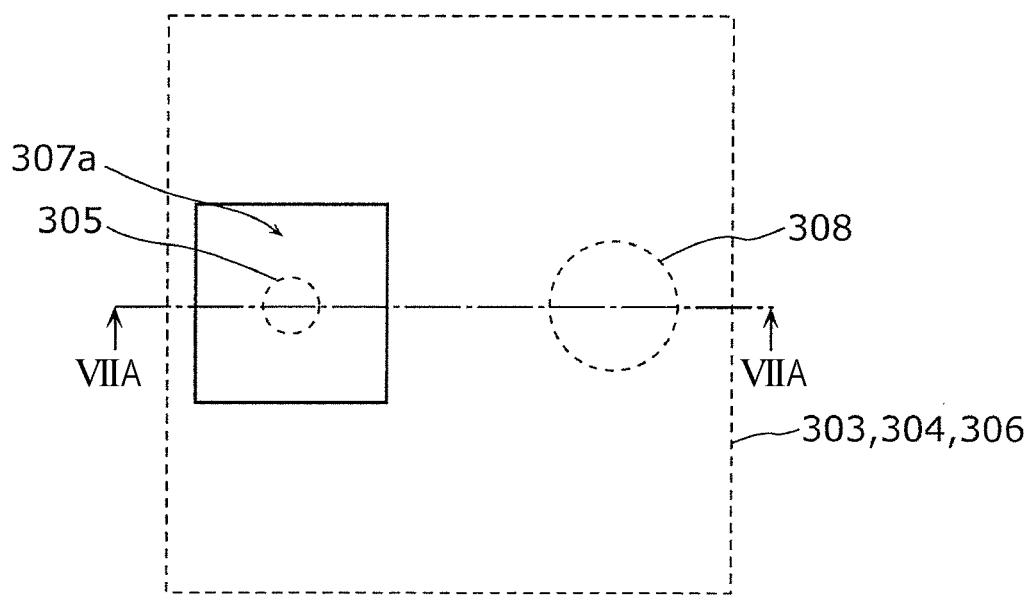
FIG. 7B is a top view illustrating the example of the structure of the hydrogen sensor according to Second Embodiment.

FIG. 7B is a top view illustrating the example of the structure of the hydrogen sensor 300 according to Second Embodiment. The cross-section shown in FIG. 7A corresponds to the cross-section viewed along the cutting line VIIA-VIIA of FIG. 7B in the arrow direction.

The hydrogen sensor 300 includes a substrate 301, an insulation film 302, a first electrode 303, a resistive film 304, a second electrode 306, an insulation film 310, an insulation film 307, a via 308, and a wiring 309. Herein, the resistive film 304 is an example of the "metal oxide layer", the insulation film 310 is an example of the "first insulation film", and the insulation film 307 is an example of the "second insulation film".

The insulation film 302 is disposed on the substrate 301. The first electrode 303 is disposed on the insulation film 302. The insulation film 310 is disposed on the second electrode 306. The insulation film 307 is disposed on the insulation film 310.

The first electrode 303 and the second electrode 306 are disposed above the insulation film 302 such that their main surfaces face each other. The resistive film 304 is disposed so as to be in contact with the main surface of the first electrode 303 and the main surface of the second electrode 306.

The insulation film 307 is provided with an opening 307a for allowing hydrogen gas contained in the gas as an object to be tested to pass through the insulation film 310 and reach the second electrode 306. In other words, the insulation film 307 covers the first electrode 303, the second electrode 306, and the resistive film 304 excluding the connection area B where the second electrode 306 and the insulation film 310 are in contact with each other. The insulation film 307 indirectly covers the second electrode 306 through the insulation film 310. The upper surface (i.e., the other surface opposite to the main surface being in contact with the second electrode 306) of the insulation film 310 is exposed in the portion facing the connection area B.

The resistive film 304 is a layer lying between the first electrode 303 and the second electrode 306 and changing the resistance value based on the electrical signal applied between the first electrode 303 and the second electrode 306. For example, the resistive film 304 reversibly transitions between a high resistive state and a low resistive state depending on the voltage (potential difference) applied between the first electrode 303 and the second electrode 306. The hydrogen sensor 300 transitions from the high resistive state to the low resistive state depending on the hydrogen gas passed through the insulation film 310 and reached the second electrode 306.

The local area 305 is disposed in the inside of the resistive film 304 so as to be in contact with the second electrode 306 and is not in contact with the first electrode 303. The degree of oxygen deficiency of the local area 305 is higher than that of its circumference (i.e., the bulk area of the resistive film 304). The degree of oxygen deficiency of the local area 305 reversibly changes depending on the electrical signal applied between the first electrode 303 and the second electrode 306. In the local area 305, the degree of oxygen deficiency changes from a low state to a high state depending on the hydrogen gas passed through the insulation film 310 and reached the second electrode 306.

The local area 305 is a minute region in which a filament (conductive path) consisting of an oxygen defect site is inferred to be generated and disappear. The change in resistance of the resistive film 304 is inferred to be caused by generation or disappearance of the filament through a redox reaction occurred in the local area 305.

The insulation film 307 is provided with the via 308 passing through the insulation film 307 and connected to the second electrode 306 in the portion covering the upper surface of the second electrode 306. The wiring 309 is disposed on the via 308.

The phenomenon of changing resistance and the mechanism of detecting hydrogen in the hydrogen sensor 300 are the same as those in the hydrogen sensors 100 and 200 of First Embodiment, and the explanations thereof are omitted.

The hydrogen sensor 300 having the structure described above can provide the same advantageous effects as those provided by the hydrogen sensors 100 and 200 described in First Embodiment.

[Manufacturing Process and Operation of Hydrogen Sensor]

An example of a process of producing the hydrogen sensor 300 will now be described with reference to FIGS. 8A to 8F.

Figure 8A:
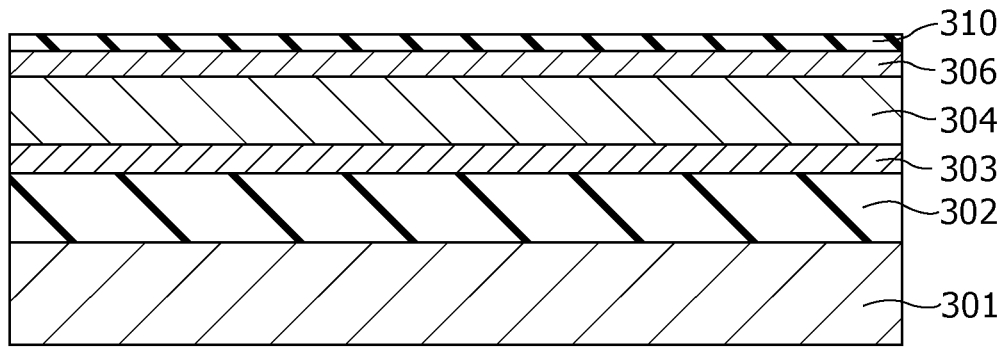
FIG. 8A is a cross-sectional view illustrating an example of a process of producing the hydrogen sensor according to Second Embodiment.

First, as shown in FIG. 8A, an insulation film 302 having a thickness of 200 nm is formed on a substrate 301, for example, of single crystal silicon by a thermal oxidation method. Subsequently, a first electrode 303 of, for example, a Pt thin film having a thickness of 100 nm is formed on the insulation film 302 by sputtering. In addition, an adhesion layer of, for example, Ti or TiN may be formed between the first electrode 303 and the insulation film 302 by sputtering. An oxygen-deficient metal oxide layer, which becomes a resistive film 304, is then formed on the first electrode 303 by reactive sputtering using, for example, a Ta target. A resistive film 304 is thus formed.

Herein, the thickness of the resistive film 304 may be, for example, about 1 nm or more and about 8 nm or less for appropriately reducing the initial resistance value and securing stable resistance change characteristics.

Subsequently, a second electrode 306 of, for example, a Pt thin film having a thickness of 150 nm is formed on the resistive film 304 by sputtering, and an insulation film 310 having a thickness ranging from 0.5 nm to 8.5 nm is deposited on the second electrode 306.

Figure 8B:
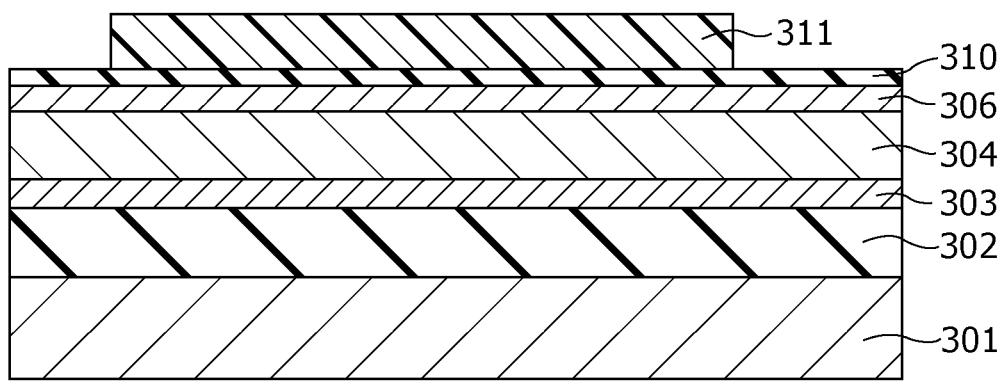
FIG. 8B is a cross-sectional view illustrating an example of the process of producing the hydrogen sensor according to Second Embodiment.
Figure 8C:
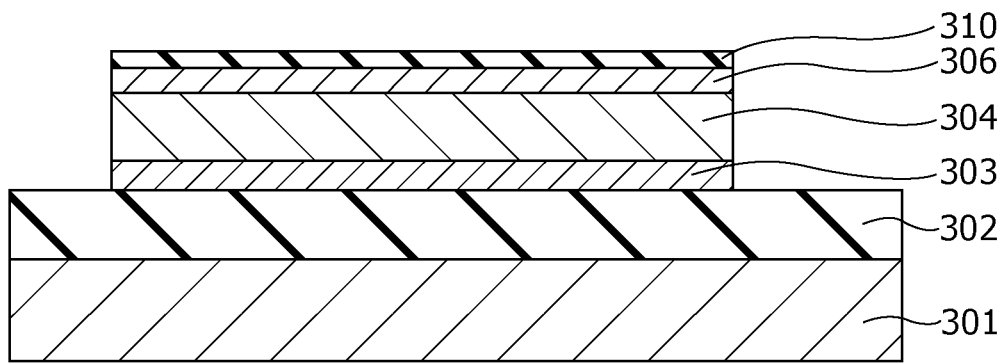
FIG. 8C is a cross-sectional view illustrating an example of the process of producing the hydrogen sensor according to Second Embodiment.

Subsequently, as shown in FIG. 8B, a photoresist mask 311 is formed by a photolithography process. Then, as shown in FIG. 8C, the first electrode 303, the resistive film 304, the second electrode 306, and the insulation film 310 are formed into the shape of the device by dry etching using the mask 311.

Figure 8D:
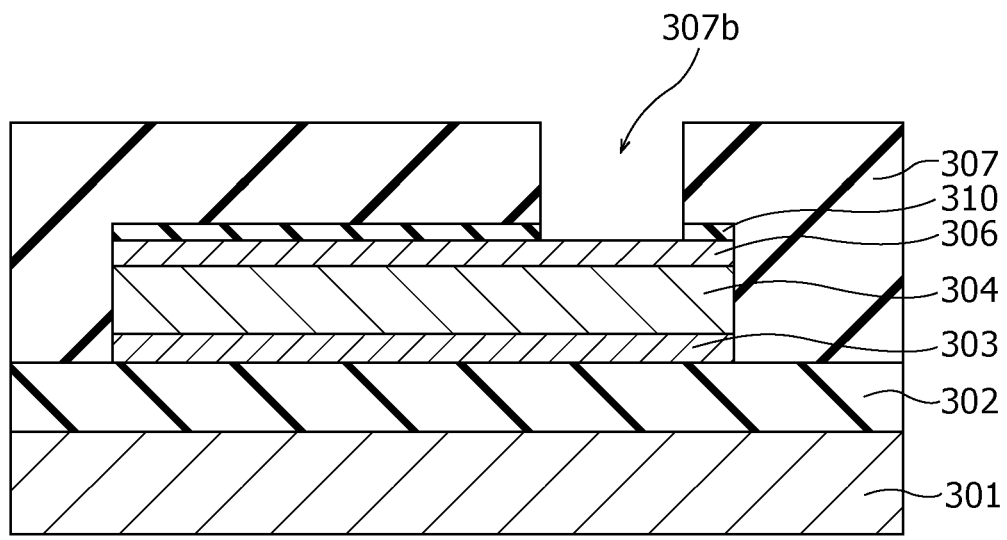
FIG. 8D is a cross-sectional view illustrating an example of the process of producing the hydrogen sensor according to Second Embodiment.

Subsequently, as shown in FIG. 8D, an insulation film 307 is formed so as to cover the insulation film 302, the first electrode 303, the resistive film 304, and the second electrode 306. A via hole 307b reaching a part of the upper surface of the second electrode 306 is then formed by etching the insulation film 307.

Figure 8E:
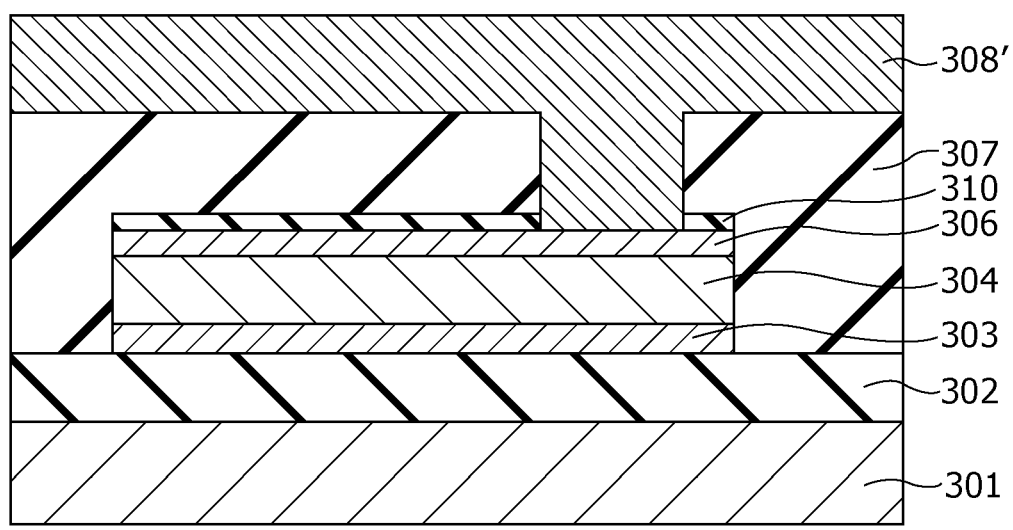
FIG. 8E is a cross-sectional view illustrating an example of the process of producing the hydrogen sensor according to Second Embodiment.
Figure 8F:
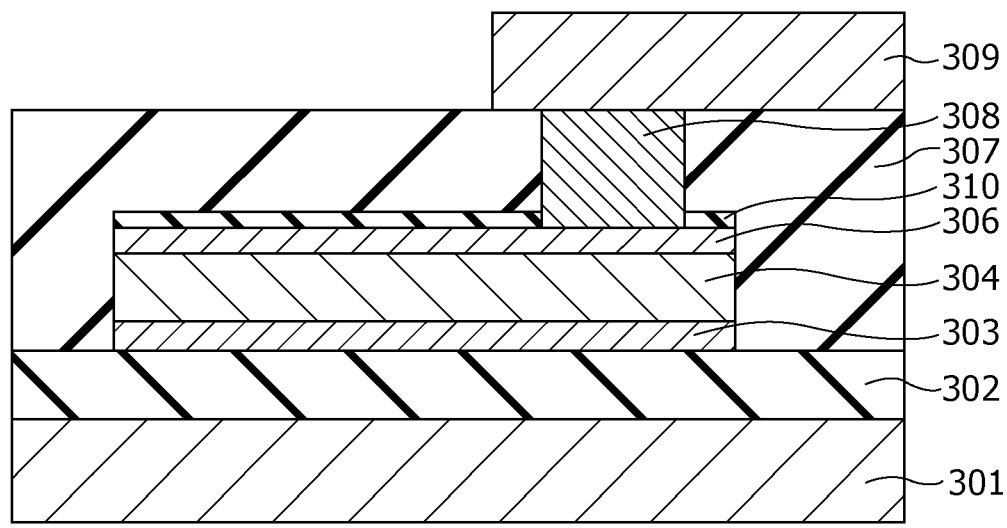
FIG. 8F is a cross-sectional view illustrating an example of the process of producing the hydrogen sensor according to Second Embodiment.

Subsequently, as shown in FIG. 8E, a conductor film 308' is formed on the upper surface of the insulation film 307 and the inside of the via hole 307b so as to fill the via hole 307b. Then, as shown in FIG. 8F, the conductor film 308' on the insulation film 307 is removed by CMP to form a via 308 in the via hole 307b. Another conductor film is further formed on the insulation film 307 and is patterned to form a wiring 309 connected to the via 308.

Figure 8G:
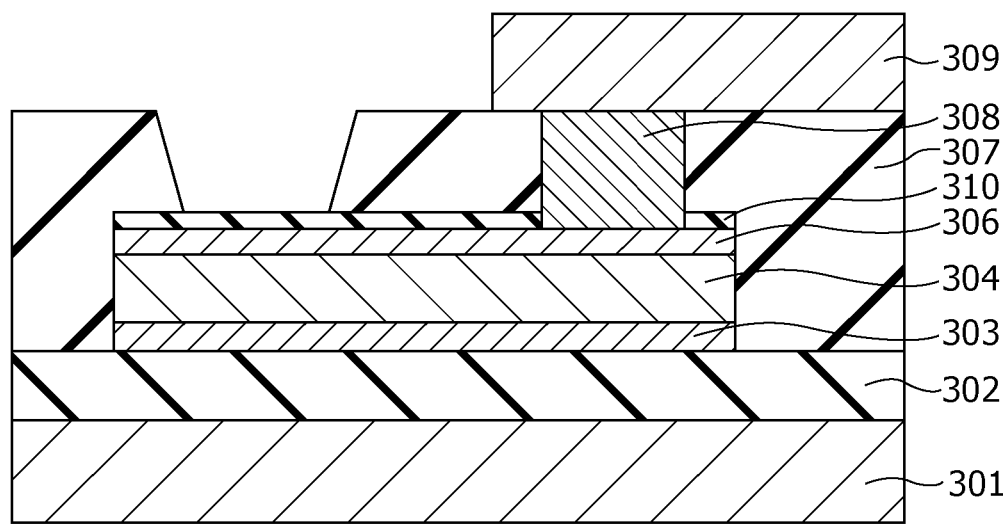
FIG. 8G is a cross-sectional view illustrating an example of the process of producing the hydrogen sensor according to Second Embodiment.

Subsequently, as shown in FIG. 8G, an opening 307a is formed by etching the insulation film 307 such that a part of the insulation film 310 formed on the upper surface of the second electrode 306 is exposed.

Subsequently, an initial break voltage is applied between the first electrode 303 and the second electrode 306 to form a local area 305 shown in FIG. 8A in the resistive film 304. A hydrogen sensor 300 is thus produced by the process described above.

The resistance change characteristics by voltage application in the hydrogen sensor 300 having the structure described above are substantially the same as those by voltage application in the hydrogen sensor 100 shown in FIG. 4. The hydrogen sensor 300 also causes a change in resistance by hydrogen gas through the same mechanism as that described in the hydrogen sensor 100 and can detect hydrogen gas with low power consumption.

[Modification]

Figure 9:
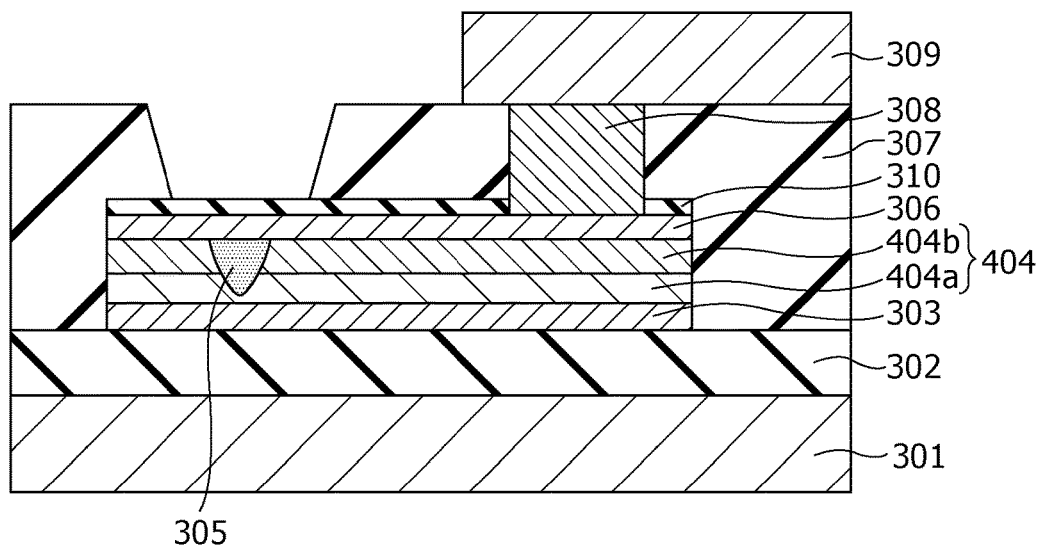
FIG. 9 is a cross-sectional view illustrating the structure of a hydrogen sensor according to a modification of Second Embodiment.

FIG. 9 is a cross-sectional view illustrating the structure of a hydrogen sensor 400 according to a modification of Second Embodiment. Only the points different from the hydrogen sensor 300 of Second Embodiment will now be described.

The hydrogen sensor 400 of the modification differs from the hydrogen sensor 300 of Second Embodiment in that the resistive film 404 includes a first metal oxide layer 404a being in contact with the first electrode 303 and a second metal oxide layer 404b being in contact with the second electrode 306.

The resistive film 404 is not limited to a layered product of two layers and may be a layered product of three or more layers.

The first metal oxide layer 404a and the second metal oxide layer 404b include a local area 305 that reversibly changes the degree of oxygen deficiency depending on application of an electric pulse and hydrogen-containing gas. The local area 305 at least passes through the second metal oxide layer 404b and is in contact with the second electrode 306. The degree of oxygen deficiency of the local area 305 is higher than that of the second metal oxide layer 404b.

In other words, the resistive film 404 has a layered structure at least composed of a first metal oxide layer 404a containing a first metal oxide and a second metal oxide layer 404b containing a second metal oxide. The first metal oxide layer 404a is disposed between the first electrode 303 and the second metal oxide layer 404b, and the second metal oxide layer 404b is disposed between the first metal oxide layer 404a and the second electrode 306.

The second metal oxide layer 404b may have a thickness smaller than that of the first metal oxide layer 404a. In such a case, a structure including the local area 305 not being in contact with the first electrode 303 can be readily formed. The degree of oxygen deficiency of the second metal oxide layer 404b may be less than that of the first metal oxide layer 404a. In such a case, the resistance value of the second metal oxide layer 404b is higher than that of the first metal oxide layer 404a. Accordingly, most of the voltage applied to the resistive film 404 is applied to the second metal oxide layer 404b. This structure is advantageous for, for example, concentrating the initial break voltage in the second metal oxide layer 404b and reducing the initial break voltage necessary for forming the local area 305.

The resistive film 404 is not limited to the case that the metals constituting the first metal oxide layer 404a and the second metal oxide layer 404b are the same, and the metals may be different from each other. That is, the first metal oxide layer 404a and the second metal oxide layer 404b may be made of different metal oxides.

If the first metal constituting the first metal oxide layer 404a and the second metal constituting the second metal oxide layer 404b are the same, the oxygen content has a corresponding relationship with the degree of oxygen deficiency. That is, when the oxygen content of the second metal oxide is higher than that of the first metal oxide, the degree of oxygen deficiency of the second metal oxide is less than that of the first metal oxide.

The resistive film 404 includes a local area 305 in the vicinity of the interface between the first metal oxide layer 404a and the second metal oxide layer 404b. The local area 305 has a degree of oxygen deficiency higher than that of the second metal oxide layer 404b and is different from that of the first metal oxide layer 404a.

The local area 305 is formed in the resistive film 404 having a layered structure of the first metal oxide layer 404a and the second metal oxide layer 404b by applying an initial break voltage between the first electrode 303 and the second electrode 306. The initial break voltage forms the local area 305 that is in contact with the second electrode 306, passes through the second metal oxide layer 404b, partially penetrates into the first metal oxide layer 404a, and is not in contact with the first electrode 303.

In the hydrogen sensors 300 and 400 having the structures described above, the insulation film 310 selectively transmits hydrogen gas, and thereby these hydrogen sensors selectively detect hydrogen gas. In addition, the hydrogen sensors can generate heat by only the current for detecting the resistive state and can detect hydrogen gas without heating with a separate heater. Thus, a hydrogen sensor having excellent power-saving properties can be given.

[Supplement]

In FIG. 7A, the hydrogen sensor 300 includes a first electrode 303, a metal oxide layer 304, a second electrode 306, a first insulation film 310, and a second insulation film 307.

The metal oxide layer 304 includes a local area 305. In the metal oxide layer 304, the area surrounding the local area 305 is called a bulk area. Herein, the term "surrounding the local area 305" is not limited to entirely surrounding the outer periphery of the local area 305. The degree of oxygen deficiency of the local area 305 is higher than that of the bulk area.

The first insulation film 310 covers the upper surface of the second electrode 306. For example, the outline of the first insulation film 310 coincides with the outline of the second electrode 306 when viewed from a direction perpendicular to the main surface of the first insulation film 310. The first insulation film 310 is, for example, a silicon oxide film, a silicon nitride film, a silicon oxynitride film, or an aluminum oxide film.

The second insulation film 307 covers the first electrode 303, the metal oxide layer 304, and the second electrode 306. The second insulation film 307 includes an opening 307a reaching the first insulation film 310. The second insulation film 307 has a thickness smaller than that of the first insulation film 310.

As shown in FIG. 7B, the local area 305 lies in the inside of the opening 307a, when viewed from a direction perpendicular to the main surface of the second electrode 306. In other words, as shown in FIG. 7A, the first insulation film 310, the second electrode 306, and the local area 305 are disposed in this order in a direction passing through the opening 307a.

In FIG. 7A, the hydrogen sensor 300 includes a conductive plug 308 passing through the second insulation film 307 and the first insulation film 310 and connected to the second electrode 306 and a wiring 309 connected to the conductive plug 308.

Third Embodiment

A fuel-cell vehicle according to Third Embodiment includes any of the hydrogen sensors described in First and Second Embodiments and their modifications. This fuel-cell vehicle detects hydrogen gas in the vehicle with the hydrogen sensor.

Figure 10:
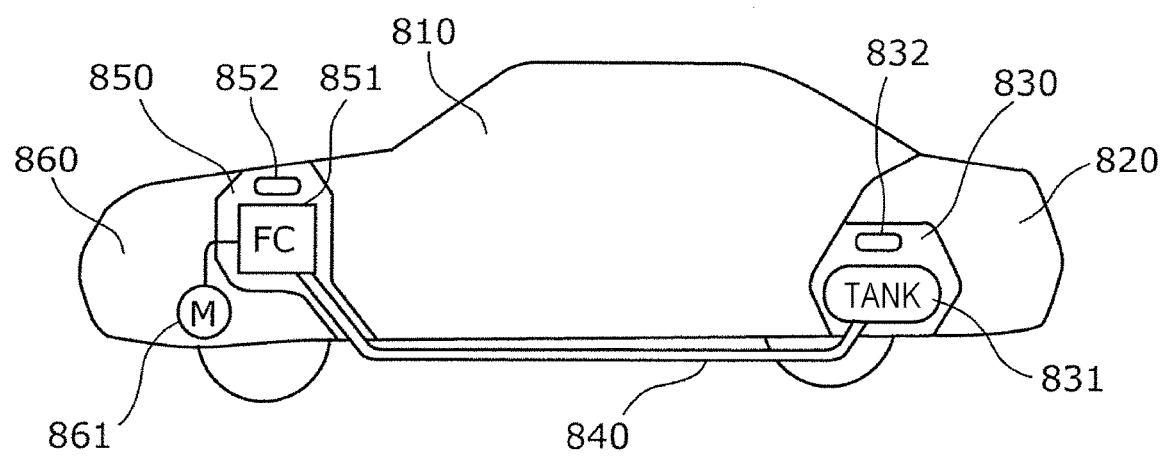
FIG. 10 is a schematic view illustrating an example of the structure of a fuel-cell vehicle according to Third Embodiment.

FIG. 10 is a side view illustrating an example of the structure of a fuel-cell vehicle 800 according to Third Embodiment.

The fuel-cell vehicle 800 includes a passenger compartment 810, a trunk 820, a gas tank chamber 830, a fuel tank 831, a hydrogen sensor 832, a pipe 840, a fuel cell chamber 850, a fuel cell 851, a hydrogen sensor 852, a motor chamber 860, and a motor 861.

The fuel tank 831 is disposed in the gas tank chamber 830 and preserves hydrogen gas as the fuel gas. The hydrogen sensor 832 detects fuel gas leakage in the gas tank chamber 830.

The fuel cell 851 is constituted as a fuel cell stack composed of stacked cells that are base units each including a fuel electrode, an air electrode, and an electrolyte. The fuel cell 851 is disposed in the fuel cell chamber 850. The hydrogen gas in the fuel tank 831 is sent into the fuel cell 851 in the fuel cell chamber 850 through the pipe 840. The fuel cell 851 generates electric power by allowing this hydrogen gas to react with oxygen gas in the atmosphere. The hydrogen sensor 852 detects hydrogen gas leakage in the fuel cell chamber 850.

The motor 861 is disposed in the motor chamber 860. The electric power generated by the fuel cell 851 rotates the motor 861, and thereby the fuel-cell vehicle 800 travels.

As described above, the hydrogen sensor according to the present disclosure can detect hydrogen gas with a very low power consumption of about 0.01 mW for example. Accordingly, the hydrogen sensor can monitor hydrogen gas leakage at all times by utilizing the excellent power-saving properties, without significantly increasing the stand-by power of the fuel-cell vehicle.

For example, a predetermined voltage may be applied at all times to the hydrogen sensors 832 and 852, regardless of the operation state of the ignition key of the fuel-cell vehicle 800. In such a case, whether hydrogen gas is present or not in the outside of the fuel tank 831 in the gas tank chamber 830 and in the outside of the fuel cell 851 in the fuel cell chamber 850 may be judged based on the amounts of the current flowing in the hydrogen sensors 832 and 852, respectively.

Accordingly, for example, since the presence or absence of hydrogen gas leakage has been already judged at the time of operating the ignition key, the start-up time of the fuel-cell vehicle can be shortened, compared to the case of judging the presence or absence of hydrogen gas leakage after operation of the ignition key. In addition, the safety can be improved by continuously monitoring hydrogen gas leakage after running of the fuel-cell vehicle, for example, even after the fuel-cell vehicle has been housed in a garage.

Other Modification

Hydrogen sensors, methods of detecting hydrogen gas, and fuel-cell vehicles according to some aspects of the present disclosure have been described based on embodiments, but the present disclosure is not limited to these embodiments. Numerous modifications of the embodiments and configurations constructed by combining components in the embodiments that can be conceived by those skilled in the art will fall within the scope of the present disclosure within a range that does not depart from the gist of the present disclosure.

For example, the hydrogen sensor described above may further include a measurement circuit for measuring the current flowing in the resistive film when a predetermined voltage is applied between the first electrode and the second electrode. The hydrogen sensor may further include a power supply circuit for applying a predetermined voltage at all times between the first electrode and the second electrode.

Such structures can provide hydrogen sensors having high convenience as module components including a measurement circuit or a power supply circuit.

The hydrogen sensors 100 and 300 may have structures for intentionally forming the local areas 105 and 305, respectively, directly under the respective connection areas A and B. For example, in the hydrogen sensors 100 and 300, needle-shaped protrusions may be provided on the upper surfaces of the first electrodes 103 and 303 lying directly under the respective connection areas A and B, respectively. In the hydrogen sensors 100 and 300, regions having resistance increased by, for example, oxidation or nitration may be formed in the resistive films 104 and 304, respectively, excluding the areas directly under the respective connection areas A and B.

Such structures can concentrate the electric fields directly under the connection areas A and B when the respective initial break voltages are applied. Accordingly, as shown in FIGS. 1A and 7A, the local areas 105 and 305 are readily formed directly under the connection areas A and B, respectively. The intentional formation of the local areas 105 and 305 directly under the respective connection areas A and B can provide hydrogen sensors having excellent characteristics of detecting hydrogen gas.

Overview of Embodiments

A hydrogen sensor according to an aspect includes first and second electrodes disposed such that main surfaces thereof face each other; a metal oxide layer disposed so as to be in contact with the main surface of the first electrode and the main surface of the second electrode; a local area disposed in the inside of the metal oxide layer so as to be in contact with the second electrode and having a degree of oxygen deficiency higher than that of the metal oxide layer; a first insulation film disposed so as to have a main surface being in contact with the other surface opposite to the above-mentioned main surface of the second electrode; and a second insulation film covering the first electrode, the second electrode, and the metal oxide layer excluding the connection area where the second electrode and the first insulation film are in contact with each other. The other surface opposite to the main surface of the first insulation film is exposed in the region facing the connection area, and the hydrogen sensor has characteristics of decreasing the resistance value between the first electrode and the second electrode by a contact of hydrogen molecules passed through the first insulation film with the second electrode.

In such a structure, the current flowing between the first electrode and the second electrode is concentrated in the local area having a high degree of oxygen deficiency. As a result, the temperature of the local area can be increased with a small amount of current. Consequently, the resulting hydrogen sensor can detect a hydrogen-containing gas utilizing the self-heating and gas sensitivity of the local area formed in the inside of the metal oxide layer without heating with a heater and thus has excellent power-saving properties.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area in the inside of the metal oxide layer to reduce the resistance value between the first electrode and the second electrode (the resistance value of the local area in the inside of the metal oxide layer).

More specifically, an increase in the temperature of the local area increases the temperature of the surface of the second electrode. This increase in the temperature enhances the efficiency of releasing hydrogen atoms from hydrogen molecules at the second electrode by the catalytic action of the second electrode.

The contact of hydrogen molecules passed through the first insulation film with the second electrode causes a release of hydrogen atoms from the hydrogen molecules. The released hydrogen atoms diffuse in the second electrode and reach the local area. The hydrogen atoms then bind to oxygen of the metal oxide present in the local area into water ($H_2O$). Consequently, the degree of oxygen deficiency of the local area is further increased. As a result, current easily flows in the local area, and the resistance between the first electrode and the second electrode decreases.

The first insulation film may selectively transmit hydrogen molecules.

In such a structure, the first insulation film selectively transmits hydrogen molecules, and thereby the hydrogen sensor can selectively detect hydrogen gas contained in the gas as an object to be tested.

The first insulation film may be a silicon oxide film.

In such a structure, the hydrogen sensor can selectively detect hydrogen gas contained in the gas as an object to be tested using the hydrogen selectivity of the silicon oxide film.

The first insulation film may have a thickness allowing transmission of hydrogen molecules in the number necessary for changing the resistance of the metal oxide layer within a predetermined time.

In such a structure, the time necessary for detecting hydrogen gas with the hydrogen sensor can be reduced within the predetermined time by appropriately regulating the thickness of the first insulation film.

The thickness of the silicon oxide film may be 8.5 nm or less.

In such a structure, a hydrogen sensor causing a change in resistance of the metal oxide layer by about 2200 hydrogen molecules reached the second electrode, which is the case actually investigated by the present inventors, can detect hydrogen gas contained in the gas as an object to be tested having a hydrogen molecule density of 0.1% within 1 second.

The thickness of the silicon oxide film may be 0.5 nm or more.

In such a structure, the electrons in the second electrode cannot substantially pass through the silicon oxide film, resulting in a reduction in the risk of deteriorating the hydrogen selectivity by interaction of electrons passed through the silicon oxide film with molecules present in the outside.

The metal oxide layer is a laminate composed of a first metal oxide layer made of a first metal oxide and a second metal oxide layer made of a second metal oxide having a degree of oxygen deficiency less than that of the first metal oxide. The first metal oxide layer is in contact with the first electrode, and the second metal oxide layer is in contact with the second electrode. The local area is formed so as to at least pass through the second metal oxide layer and be in contact with the second electrode and may have a degree of oxygen deficiency higher than that of the second metal oxide layer.

In such a structure, the employment of the layered structure having excellent resistance change characteristics as the metal oxide layer can provide a hydrogen sensor having excellent characteristics of detecting hydrogen gas.

The second electrode may be made of a material having a catalytic action for releasing hydrogen atoms from the hydrogen molecules.

In such a structure, hydrogen atoms are released from the hydrogen molecules in the portion of the second electrode being in contact with the local area. The released hydrogen atoms bind to oxygen atoms in the local area formed in the inside of the metal oxide layer to reduce the resistance value of the local area and reduce the resistance value between the first electrode and the second electrode.

The second electrode may be made of platinum or palladium.

In such a structure, the second electrode can release hydrogen atoms from the hydrogen molecules by the catalytic action of platinum or palladium.

The first metal oxide and the second metal oxide may be each independently a transition metal oxide or aluminum oxide.

In such a structure, the hydrogen sensor can have excellent characteristics of detecting hydrogen gas by using a transition metal oxide or aluminum oxide having excellent resistance change characteristics independently as each of the first metal oxide and the second metal oxide.

The transition metal oxide may be any of tantalum oxide, hafnium oxide, and zirconium oxide.

In such a structure, the hydrogen sensor can have excellent characteristics of detecting hydrogen gas by using tantalum oxide, hafnium oxide, or zirconium oxide having excellent resistance change characteristics as the transition metal oxide.

The metal oxide layer may reversibly transition between a high resistive state and a low resistive state having a resistance value less than that of the high resistive state based on the voltage applied between the first electrode and the second electrode.

In such a structure, transition of the resistive state of the metal oxide layer can be electrically performed, in addition to the transition by hydrogen gas. For example, the gas as an object to be tested may be brought into contact with the insulation film after setting of the metal oxide layer to an electrically high resistive state. In such a case, a reduction in the resistance value can be clearly detected to enhance the characteristics of detecting hydrogen gas.

In addition to the connection area, the first insulation film may be disposed on at least a part of the above-described other surface of the second electrode excluding the connection area.

In such a structure, the process of producing the hydrogen sensor can be simplified.

The hydrogen sensor may further include a measurement circuit for measuring the current flowing in the metal oxide layer when a predetermined voltage is applied between the first electrode and the second electrode.

The hydrogen sensor may further include a power supply circuit for applying a predetermined voltage at all times between the first electrode and the second electrode.

Such a structure can provide a hydrogen sensor having high convenience as a module component including a measurement circuit or a power supply circuit. In particular, hydrogen gas leakage can be continuously monitored with a slight amount of power by utilizing the power-saving properties of the hydrogen sensor.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area of the metal oxide layer. The resistance value of the metal oxide layer may be thus reduced.

In such a structure, the current flowing between the first electrode and the second electrode is concentrated in the local area having a high degree of oxygen deficiency. As a result, the temperature of the local area can be increased with a small amount of current. Consequently, the resulting hydrogen sensor can detect a hydrogen-containing gas utilizing the self-heating and gas sensitivity of the local area formed in the inside of the metal oxide layer without heating with a heater and thus has excellent power-saving properties.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area of the metal oxide layer to reduce the resistance value between the first electrode and the second electrode.

More specifically, an increase in the temperature of the local area increases the temperature of the surface of the second electrode. This increase in the temperature enhances the efficiency of releasing hydrogen atoms from gas molecules including hydrogen atoms at the second electrode by the catalytic action of the second electrode.

The contact of hydrogen molecules containing hydrogen atoms passed through the first insulation film with the second electrode causes a release of hydrogen atoms from the hydrogen molecules. The released hydrogen atoms diffuse in the second electrode and reach the local area. The hydrogen atoms then bind to oxygen of the metal oxide present in the local area into water. Consequently, the degree of oxygen deficiency of the local area is further increased. As a result, current easily flows in the local area, and the resistance between the first electrode and the second electrode decreases.

A via passing through the second insulation film and connected to the second electrode may be disposed in the portion of the second insulation film covering the above-described other surface of the second electrode, and a conductor connected to the via may be disposed.

In such a structure, the area of the connection area where the second insulation film is precluded for the contact of the gas as an object to be tested can be maintained, and the conductor can be electrically connected to the second electrode using the portion where the second insulation film is disposed.

The method of detecting hydrogen according to an aspect uses a hydrogen sensor. The hydrogen sensor includes first and second electrodes disposed such that main surfaces thereof face each other; a metal oxide layer disposed so as to be in contact with the main surface of the first electrode and the main surface of the second electrode; a local area disposed in the inside of the metal oxide layer so as to be in contact with the second electrode and having a degree of oxygen deficiency higher than that of the metal oxide layer; and an insulation film disposed so as to be in contact with the other surface opposite to the main surface of the second electrode. In the method of detecting hydrogen, gas containing hydrogen gas is brought into contact with the portion facing the connection area of the insulation film being in contact with the second electrode to reduce the resistance value between the first electrode and the second electrode; and the hydrogen gas is detected through the reduction.

In such a method, hydrogen can be detected with excellent power-saving properties with the hydrogen sensor generating heat by only the current for detecting the resistive state and detecting hydrogen gas without heating with a separate heater. The hydrogen sensor can selectively detect hydrogen gas in the combustible gas by using a material having characteristics of selectively transmitting hydrogen gas for the insulation film.

The fuel-cell vehicle according to an aspect includes the hydrogen sensor in at least one of a gas tank chamber accommodating a tank of hydrogen gas and a fuel cell chamber accommodating a fuel cell.

In such a structure, fuel gas leakage can be monitored at all times by utilizing the excellent power-saving properties of the hydrogen sensor, without significantly increasing the stand-by power of the fuel-cell vehicle.

For example, since the presence or absence of fuel gas leakage has been already judged at the time of operating the ignition key, the start-up time of the fuel-cell vehicle can be shortened, compared to the case of driving the hydrogen sensor for judging the presence or absence of fuel gas leakage after operation of the ignition key. In addition, the safety can be improved by continuously monitoring fuel gas leakage after running of the fuel-cell vehicle, for example, even after the fuel-cell vehicle has been housed in a garage.

The method of detecting hydrogen according to an aspect judges whether hydrogen gas is present or not in at least one of the outside of the tank in the gas tank chamber and the outside of the fuel cell in the fuel cell chamber of the fuel-cell vehicle based on the amount of the current flowing in the hydrogen sensor by applying a predetermined voltage to the hydrogen sensor at all times.

In such a method, fuel gas leakage can be monitored at all times by utilizing the excellent power-saving properties of the hydrogen sensor, without significantly increasing the stand-by power of the fuel-cell vehicle.

For example, since the presence or absence of fuel gas leakage has been already judged at the time of operating the ignition key, the start-up time of the fuel-cell vehicle can be shortened, compared to the case of driving the hydrogen sensor for judging the presence or absence of fuel gas leakage after operation of the ignition key. In addition, the safety can be improved by continuously monitoring fuel gas leakage after running of the fuel-cell vehicle, for example, even after the fuel-cell vehicle has been housed in a garage.

The hydrogen sensor according to the present disclosure can be used in, for example, a fuel-cell vehicle.

What is claimed is:

1. A hydrogen sensor comprising:
    a first electrode;
    a second electrode;
    a metal oxide layer disposed between the first electrode and the second electrode, the metal oxide layer including a bulk area and a local area surrounded by the bulk area, a degree of oxygen deficiency of the local area being higher than that of the bulk area;
    a first insulation film covering the first electrode, the second electrode, and the metal oxide layer, the first insulation film having an opening reaching the second electrode; and
    a second insulation film being in contact with the second electrode in the opening,
    wherein:
    an upper surface of the local area and an upper surface of the bulk area are in direct contact with a bottom surface of the second electrode, and
    a bottom of the local area does not directly contact an upper surface of the first electrode, wherein the bulk area is configured to generate the local area when voltage is applied to the electrodes.

2. The hydrogen sensor according to claim 1, wherein
    the second insulation film has a thickness smaller than that of the first insulation film; and
    the second insulation film is further in contact with an upper surface of the first insulation film and an inner peripheral surface of the opening.

3. The hydrogen sensor according to claim 1, wherein the local area is located inside the opening, when viewed from a direction perpendicular to a surface of the second electrode.

4. The hydrogen sensor according to claim 1, wherein the second insulation film is a silicon oxide film, a silicon nitride film, a silicon oxynitride film, or an aluminum oxide film.

5. The hydrogen sensor according to claim 1, wherein the metal oxide layer includes:

a first metal oxide layer being in contact with the first electrode, a degree of oxygen deficiency of the first metal oxide layer being higher than that of the bulk area; and a second metal oxide layer being in contact with the second electrode, the second metal oxide layer including the bulk area, and the local area is in contact with the second electrode and passes through the second metal oxide layer.

6. The hydrogen sensor according to claim 1, wherein a resistance value of the metal oxide layer reversibly changes based on application of a voltage between first electrode and the second electrode.

7. The hydrogen sensor according to claim 1, wherein the first insulation film and the second insulation film are made of the same material.

8. The hydrogen sensor according to claim 1, wherein the second electrode has a catalytic action for releasing hydrogen atoms from hydrogen molecules.

9. The hydrogen sensor according to claim 8, wherein the second electrode contains platinum or palladium.

10. The hydrogen sensor according to claim 1, wherein the metal oxide layer contains at least one selected from the group consisting of transition metal oxides and aluminum oxide.

11. The hydrogen sensor according to claim 10, wherein the metal oxide layer is at least one selected from the group consisting of tantalum oxide, hafnium oxide, zirconium oxide, and aluminum oxide.

12. The hydrogen sensor according to claim 1, wherein a resistance value between the first electrode and the second electrode is lowered when a predetermined amount of hydrogen molecules come into contact with the second electrode through the second insulation film.

13. The hydrogen sensor according to claim 12, wherein the second insulation film is a silicon oxide film.

14. The hydrogen sensor according to claim 13, wherein the silicon oxide film has a thickness of 8.5 nm or less.

15. The hydrogen sensor according to claim 14, wherein the silicon oxide film has a thickness of 0.5 nm or more.

16. A hydrogen sensor comprising:
a first electrode;
a second electrode;
a metal oxide layer disposed between the first electrode and the second electrode, the metal oxide layer including a bulk area and a local area surrounded by the bulk area, a degree of oxygen deficiency of the local area being higher than that of the bulk area;
a first insulation film opposed to the metal oxide layer across the second electrode; and
a second insulation film covering the first electrode, the second electrode, the metal oxide layer, and the first insulation film, the second insulation film having an opening reaching the first insulation film,
wherein:
an upper surface of the local area and an upper surface of the bulk area are in direct contact with a bottom surface of the second electrode, and
a bottom of the local area does not directly contact an upper surface of the first electrode, wherein the bulk area is configured to generate the local area when voltage is applied to the electrodes.

17. A method of detecting hydrogen with a hydrogen sensor,
the hydrogen sensor comprising:
a first electrode;
a second electrode;
a metal oxide layer disposed between the first electrode and the second electrode, the metal oxide layer including a bulk area and a local area surrounded by the bulk area, a degree of oxygen deficiency of the local area being higher than that of the bulk area;
a first insulation film covering the first electrode, the second electrode, and the metal oxide layer, the first insulation film having an opening reaching the second electrode; and
a second insulation film being in contact with the second electrode in the opening,
wherein an upper surface of the local area and an upper surface of the bulk area are in direct contact with a bottom surface of the second electrode, and
a bottom of the local area does not directly contact an upper surface of the first electrode, wherein the bulk area is configured to generate the local area when voltage is applied to the electrodes,
the method of detecting hydrogen comprising:
allowing gas to come into contact with the second insulation film that is contact with the second electrode; and
detecting a reduction in a resistance value between the first electrode and the second electrode to detect hydrogen gas contained in the gas.

18. A method of detecting hydrogen with a hydrogen sensor,
the hydrogen sensor comprising:
a first electrode;
a second electrode;
a metal oxide layer disposed between the first electrode and the second electrode, the metal oxide layer including a bulk area and a local area surrounded by the bulk area, a degree of oxygen deficiency of the local area being higher than that of the bulk area;
a first insulation film opposed to the metal oxide layer across the second electrode; and
a second insulation film covering the first electrode, the second electrode, the metal oxide layer, and the first insulation film, the second insulation film having an opening reaching the first insulation film,
wherein an upper surface of the local area and an upper surface of the bulk area are in direct contact with a bottom surface of the second electrode, and
a bottom of the local area does not directly contact an upper surface of the first electrode, wherein the bulk area is configured to generate the local area when voltage is applied to the electrodes,
the method of detecting hydrogen comprising:
allowing gas to come into contact with the first insulation film through the opening; and
detecting a reduction in a resistance value between the first electrode and the second electrode to detect hydrogen gas contained in the gas.

* * * * *